(12) United States Patent
Hochman et al.

(10) Patent No.: US 6,241,672 B1
(45) Date of Patent: *Jun. 5, 2001

(54) METHOD AND APPARATUS FOR OPTICALLY IMAGING SOLID TUMOR TISSUE

(75) Inventors: Daryl Hochman; Michael M. Haglund, both of Seattle, WA (US)

(73) Assignee: University of Washington, Seattle, WA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/993,733

(22) Filed: Dec. 18, 1997

Related U.S. Application Data

(63) Continuation of application No. 08/477,468, filed on Jun. 7, 1995, now Pat. No. 5,699,798, which is a continuation-in-part of application No. 08/073,353, filed on Jun. 7, 1993, now Pat. No. 5,465,718, which is a continuation-in-part of application No. 07/894,270, filed on Jun. 8, 1992, now Pat. No. 5,438,989, which is a continuation-in-part of application No. 07/565,454, filed on Aug. 10, 1990, now Pat. No. 5,215,095.

(51) Int. Cl.[7] ....................................... A61B 5/00
(52) U.S. Cl. ............................. 600/431; 348/77
(58) Field of Search ..................... 600/407, 473, 600/476, 431, 475, 477; 348/68, 77, 164; 382/128

(56) References Cited

U.S. PATENT DOCUMENTS

| | | | |
|---|---|---|---|
| 4,170,987 | * 10/1979 | Anselmo et al. | |
| 4,541,438 | * 9/1985 | Parker et al. | |
| 4,693,255 | * 9/1987 | Beall | |
| 4,768,513 | * 9/1988 | Suzuki | |
| 4,947,850 | * 8/1990 | Vanderkooi et al. | |
| 5,036,853 | * 8/1991 | Jeffcoat et al. | |
| 5,074,306 | * 12/1991 | Green et al. | 128/664 |
| 5,111,821 | * 5/1992 | Potter | 128/654 |
| 5,201,318 | * 4/1993 | Rava et al. | |
| 5,239,998 | * 8/1993 | Krauthamer | |
| 5,363,854 | * 11/1994 | Martens et al. | |
| 5,438,989 | * 8/1995 | Hochman et al. | |
| 5,465,718 | * 11/1995 | Hochman et al. | |
| 5,699,798 | * 12/1997 | Hochman et al. | |
| 5,769,792 | * 6/1998 | Palcic et al. | |

\* cited by examiner

*Primary Examiner*—Marvin M. Lateef
*Assistant Examiner*—Shawna J Shaw
(74) *Attorney, Agent, or Firm*—Ann W. Speckman

(57) ABSTRACT

The present invention provides a method for determining the presence of solid tumor tissue, for identifying and mapping the margins of solid tumors during surgical or diagnostic procedures, and for grading and characterizing tumor tissue by detecting changes in the optical properties of an area of interest suspected to contain tumor tissue.

40 Claims, 11 Drawing Sheets

METHOD AND APPARATUS FOR OPTICALLY IMAGING SOLID TUMOR TISSUE

CROSS REFERENCE TO RELATED APPLICATIONS

This patent application is a continuation of application Ser. No. 08/477,468, filed Jun. 7, 1995, issued Dec. 23, 1997 as U.S. Pat. No. 5,699,798, which is a continuation-in-part of U.S. patent application Ser. No. 08/073,353, filed Jun. 7, 1993 and issued as U.S. Pat. No. 5,465,718, which is a continuation-in-part of U.S. patent application Ser. No. 07/894,270, filed on Jun. 8, 1992 and issued as U.S. Pat. No. 5,438,989, which is a continuation-in-part of U.S. patent application Ser. No. 07/565,454 filed on Aug. 10, 1990 and issued as U.S. Pat. No. 5,215,095, all of which are incorporated herein by reference in their entirety.

TECHNICAL FIELD OF THE INVENTION

The present invention relates to methods and apparatus for optically imaging tumor tissue. More specifically, the methods and apparatus of the present invention may be used to distinguish tumor tissue from normal tissue and to grade and characterize tumor tissue.

BACKGROUND OF THE INVENTION

A primary goal of surgical treatment of tumors is the complete removal of abnormal or pathological tissue while sparing normal areas. Hence, a surgeon attempts to distinguish abnormal tissue from adjacent areas of normal tissue and to identify boundaries of pathological tissue so that pathological tissue may be removed without affecting surrounding areas. For example, when removing tumors from the cortex, it is important that substantially all the pathological tissue be removed while minimizing damage to cortical tissue committed to important functions, such as language, motor and sensory areas.

Incidence rates for primary intracranial brain tumors are in the range of 50–150 cases per million population or about 18,000 cases per year. Approximately one half of brain tumors are malignant. Malignant brain tumors in adults occur predominantly in the age range of 40–55 years while the incidence of more benign tumors peaks near 35 years of age. A primary means for treatment of such tumors is surgical removal. Many studies have shown that clinical outcome is improved when more of the total amount of tumor tissue is removed. For gross total resections of tumors, the 5-year survival rate is doubled when compared to subtotal resection. Both duration of survival and independent status of the patient are prolonged when the extent of resection is maximized in malignant gliomas. Current intraoperative techniques do not provide rapid differentiation of tumor tissue from normal brain tissue, especially once the resection of the tumor begins. Development of techniques that enhance the ability to identify tumor tissue intraoperatively may result in maximizing the degree of tumor resection, thereby prolonging survival.

Of the 500,000 patients projected to die of systemic cancer per year in the United States, approximately 25%, or over 125,000, can be expected to have intracranial metastasis. The primary focus for surgery in this group is those patients with single lesions who do not have widespread or progressive cancer. This group represents about 20–25% of patients with metastases (30,000), however, the actual number of patients that are good candidates for surgery is slightly smaller. Currently, of those patients undergoing surgery, one half will have local recurrence of their tumor at the site of operation, while the other half will develop a tumor elsewhere. The fact that about 50% of the surgeries fail at the site of operation means that an improved ability to remove as much tumor as possible by detecting and localizing tumor margins during tumor removal could potentially decrease the incidence of local recurrence.

Thus, for both primary and metastatic tumors, the more tumor tissue removed, the better the outcome and the longer the survival. Further, by maximizing the extent of resection, the length of functional, good quality survival is also increased.

Most current tumor imaging techniques are performed before surgery to provide information about tumor location. Presurgery imaging methods include magnetic resonance imaging (MRI) and computerized tomography (CT). In the operating room, only intraoperative ultrasound and stereotaxic systems can provide information about the location of tumors. Ultrasound shows location of the tumor from the surface, but, once surgery begins, does not provide information to the surgeon necessary to prevent destruction of important functional tissue while permitting maximal removal of tumor tissue. Stereotaxic systems coupled with advanced imaging techniques have (at select few hospitals) been able to localize tumor margins based upon the preoperative CT or MRI scans. However, studies have shown that the actual tumor extends 2–3 cm beyond where the image enhanced putative tumor is located on preoperative images. Therefore, the only reliable method currently available for determining the location of tumors is to obtain multiple biopsies during surgery and wait for results of microscopic examination of frozen sections. This technique, known as multiple histological margin sampling, suffers several drawbacks. First, this is a time-consuming procedure and can add about 30 to 90 minutes (depending upon the number of samples taken) to the length of time the patient is under anesthesia. The increased time required for margin sampling leads to increased medical costs, as operating room time costs are high. Moreover, increased operating room time for the patient increases the probability of infection. Multiple histological margin sampling is prone to errors, as the pathologist must prepare and evaluate samples in short order. In addition, margin sampling does not truly evaluate all regions surrounding a primary tumor and some areas of residual tumor can be missed due to sampling error. Thus, although patient outcome is dependent upon aggressive removal of tumor tissue, a surgeon must often rely upon an estimation technique as a guide. Surgeons must make difficult decisions between aggressively removing tissue and destroying surrounding functional tissue, and may not know the true outcome of the procedure until permanent tissue sections are available about one week later. Consequently, an additional surgical procedure may be required.

Other techniques developed to improve imaging of solid tumor masses during surgery include determining the shape of visible luminescence spectra from normal and cancerous tissue. U.S. Pat. No. 4,930,516 teaches that the shape of visible luminescence spectra from normal and cancerous tissue are different. Specifically, there is a shift to blue with different luminescent intensity peaks in cancerous tissue as compared to normal tissue. Thus it is possible to distinguish cancerous tissue by exciting the tissue with a beam of ultraviolet (UV) light and comparing visible native luminescence emitted from the tissue with luminescence from a non-cancerous control of the same tissue type. Such a procedure is fraught with difficulties since a real time, spatial map of the tumor location is not provided for the use of a surgeon. Moreover, the use of UV light as an excitation wavelength can cause photodynamic changes to normal cells and is dangerous for use in an operating room. In addition, UV light penetrates only superficially into tissue and requires quartz optical components instead of glass.

Optical imaging of tissue using techniques and apparatus similar to those described herein is described in U.S. Pat. Nos. 5,699,798, 5,465,718 and 5,419,989, all of which are incorporated herein by reference in their entirety.

Therefore, there remains a need in the art for a more effective method and device for determining solid tumor locations and precisely mapping tumor margins in a real-time mode during surgery. Such a method and device should further be useful for inexpensive evaluation of any solid tumor by a non-invasive procedure (e.g., breast mammography) and be capable of grading and characterizing tumors.

SUMMARY OF THE INVENTION

The methods and device described herein can be used to optically distinguish between tumor and non-tumor tissue, and to image margins and dimensions of solid tumors during surgical or diagnostic procedures. In addition, the methods and device of the present invention can be used to grade and characterize solid tumor tissue, thereby distinguishing malignant from non-malignant tumor tissue. For example, optical imaging techniques of the present invention can be used by a surgeon intraoperatively to distinguish between tumor and non-tumor tissue with a high degree of spatial resolution. Although the optical imaging techniques disclosed herein are used principally for in vivo applications, they may also be used to distinguish between tumor and non-tumor tissue in in vitro preparations. The optical imaging techniques can be used to provide information in "real-time" and therefore can be employed intraoperatively.

While the methods and apparatus of the present invention may be employed to optically image tumor tissue without the use of dyes or contrast-enhancing agents, use of such agents provides images with higher resolution and is therefore preferred. The dynamics of dye perfusion through normal tissue differ from those through tumor tissue. Thus, using the methods and apparatus described herein, it is possible to differentiate tumor tissue from surrounding normal tissue by monitoring the changes in optical properties is resulting from the different kinetics of dye uptake in tumor tissue compared to normal tissue.

Dyes suitable for use in the present invention include fluorescent and phosphorescent materials, dyes that bind to cell membranes, optical probes that preferentially accumulate in tumor tissue, phase resonance dye pairs, and the like. Examples of appropriate dyes include indocyanines, fluoresceins, hematoporphyrins, and fluoresdamines. A preferred dye is indocyanine green which has a broad absorption wavelength range and a peak absorption in the range of 730 nm to 840 nm. Detectors appropriate for use with such dyes, or contrast enhancing agents, are well known in the art.

The apparatus of the present invention employs an electromagnetic radiation (emr) source for uniformly illuminating an area of interest (i.e., an area believed to contain solid tumor tissue), and an optical detector capable of detecting and acquiring data relating to one or more optical properties of the area of interest. In a simple form, the apparatus of the present invention may include an optical fiber operably connected to an emr source that illuminates tissue, and another optical fiber operably connected to an optical detector, such as a photodiode, that detects one or more optical properties of the illuminated tissue. The detector is used to obtain control data representing the "normal" or "background" optical properties of an area of interest, and to obtain subsequent data representing the optical properties of an area of interest following administration of an image-enhancing dye, or during a monitoring interval. The subsequent data is compared to the control data to identify changes in optical properties representative of uptake of dye by tumor tissue. According to a preferred embodiment, the control, subsequent and comparison data are presented in a visual format as images.

Various types of optical detectors may be used, depending on the optical property being detected, the format of data being collected, certain properties of the area of interest, and the type of application, e.a., intraoperative, diagnostic, monitoring, or the like. In general, any type of photon detector may be utilized as an optical detector. The optical detector generally includes photon sensitive elements and optical elements that enhance or process the detected optical signals. Numerous optical detectors are known and may be used or adapted for use in the methods and apparatus of the present invention.

Changes in optical properties that may be indicative of changes of dye perfusion and therefore differentiate tumor from non-tumor tissue include, for example, reflection, refraction, diffraction, absorption, scattering, birefringence, refractive index, Kerr effect, and the like. The optical detection system may be incorporated in an apparatus for use external to the area of interest, or optical detection components may be mounted in an invasive or semi-invasive system, such as an endoscope, laparoscope or the like.

Numerous devices for acquiring, processing and displaying data representative of one or more optical properties of an area of interest can be employed. One preferred device is a video camera that acquires control and subsequent images of an area of interest that can then be compared to identify areas of tumor tissue. Examination of images provides precise spatial location of tumors and permits gradation and characterization of tumor tissue. Apparatus suitable for obtaining such images have been described in the patents incorporated herein by reference and are more fully described below. For most surgical and diagnostic uses, the optical detector preferably provides images having a high degree of spatial resolution at a magnification sufficient to precisely locate the margins of a tumor. Several images are preferably acquired over a predetermined time period and combined, such as by averaging, to provide control and subsequent images for comparison.

Various data processing techniques may be advantageously used to assess the data collected in accordance with the present invention. Comparison data may be assessed or presented in a variety of formats. Processing may include averaging or otherwise combining a plurality of data sets to produce control, subsequent or comparison data sets. Images are preferably converted from an analog to a digital form for processing, and back to an analog form for display.

Data processing may also include amplification of certain signals or portions of a data set (e.g., areas of an image) to enhance the contrast seen in data set comparisons, and to thereby identify areas of tumor tissue with a high degree of spatial resolution. For example, according to one embodiment, images are processed using a transformation in which image pixel brightness values are remapped to cover a broader dynamic range of values. A "low" value may be selected and mapped to zero, with all pixel brightness values at or below the low value set to zero, and a "high" value may be selected and mapped to a selected value, with all pixel brightness values at or above the high value mapped to the high value. Pixels having an intermediate brightness value, representing the dynamic changes in brightness indicative of changes in dye perfusion, may be mapped to linearly or logarithmically increasing brightness values. This type of processing manipulation is frequently referred to as a "histogram stretch" and can be used according to the present invention to enhance the contrast of data sets, such as images, representing differences in tissue type.

Data processing techniques may also be used to manipulate data sets to provide more accurate combined and comparison data. For example, patient movement, respiration, heartbeat or reflex activity may shift an area of interest during detection of optical properties and data collection. It is important that corresponding data points in data sets (such as corresponding areas of an image) are precisely aligned to provide accurate combined and comparison data. Such alignment may be accomplished manually by a practitioner having specialized skill and expertise, or using a variety of mathematical means. Optical markers may be fixed at an area of interest and detected as the data is collected to aid in manual alignment or mathematical manipulation. Various processing techniques are described below and in the patents incorporated herein by reference.

Inaccuracies and artifacts caused by patient movement during acquisition of data can be reduced by mechanical means. According to a preferred embodiment, the emr source and the optical detector are provided as an integral unit that is mountable to a patient during detection. For example, cranial posts may be used to mount an integrated emr source/detector unit for localizing or mapping areas of cortical tumor tissue. Likewise, an integrated unit including an emr source and an optical detector may be mounted in a relatively "fixed" condition in proximity to other areas of interest.

Comparison data may be displayed in a variety of ways. For example, comparison data may be displayed in a graphical format that highlights optical differences indicative of tumor tissue. A preferred technique for presenting and displaying comparison data is in the form of visual images or photographic frames corresponding to the area of interest. This format provides a visualizable spatial location (two- or three-dimensional) of tumor tissue that is useful for treatment, diagnosis and monitoring. To enhance and provide better visualization of contrast between tumor and normal tissue, comparison images may be processed to provide an enhanced contrast grey scale or even a color image. A look up table ("LUT") may be provided, for example, that converts the gray scale values for each pixel to a different (higher contrast) gray scale value, or to a color value. Color values may map to a range of grey scale values, or color may be used to distinguish between positive-going and negative-going optical changes. In general, color-converted images provide higher contrast images that highlight changes in optical properties representing areas of tumor and normal tissue.

In operation, an area of interest in a patient is illuminated with electromagnetic radiation (emr) while one or a series of data points or data sets representing one or more optical properties of the area of interest is acquired. This data represents the control, or background, data. A series of data sets is preferably combined, for example by averaging, to obtain a control data set. The control data set is stored for comparison with data collected subsequently.

A subsequent data set representing the corresponding optical property is acquired during a subsequent time period following administration of a dye by bolus injection into vasculature circulating to the area of interest. A series of subsequent data sets is preferably combined, for example by averaging, to obtain a subsequent data set. The subsequent data set is compared with the control data set to obtain a comparison data set, preferably a difference data set. Comparison data sets can then be examined for evidence of changes in optical properties representative of areas of tumor versus non-tumor tissue within the area of interest.

The methods and apparatus described herein may be employed to obtain three-dimensional information of an area of interest suspected to contain tumor tissue by: (a) illuminating the area of interest with a least two different wavelengths of emr; (b) obtaining a sequence of control data sets corresponding to each wavelength of emr; (c) administering a dye; (d) obtaining a sequence of subsequent data sets for each wavelength of emr; (e) obtaining a series of comparison data sets for each wavelength of light by subtracting the control data set from the subsequent data set or alternatively, in the case of fluorescent dyes, subtracting the subsequent image from the control image; and (f) obtaining an enhanced comparison data set by ratioing the first comparison data set to the second comparison data set. Preferably, the area of interest is illuminated with monochromatic emr from a laser source.

BRIEF DESCRIPTION OF THE DRAWINGS

The methods and apparatus of the present invention will be described in greater detail below with reference to the following figures.

In FIG. 1A the lettered labels placed upon the brain by the surgeon overlay the tumor as identified intraoperatively by ultrasound. FIG. 1B shows a difference image taken approximately 15 seconds after intravenous injection of dye (indocyanine green at 1 mg/kg). FIG. 1C shows the difference image about 30 seconds after dye administration. The area of the tumor tissue showed the first tissue staining. FIG. 1D shows that with this low grade tumor, all tissue (both normal and abnormal) showed staining at 45 sec after dye administration. FIG. 1E is an image of the area of interest one minute after dye administration and FIG. 1F is the image five minutes after dye administration, showing complete clearance in this low grade tumor.

FIG. 2A is a grayscale image, taken before dye injection, showing that malignant brain tumor tissue was densest in the center and to the right but that the tissue elsewhere was mostly normal. This was confirmed by pathology slides and flow cytometry data available one week after surgery. FIG. 2B is the difference image at 15 seconds after intravenous injection of indocyanine green, showing that the dynamics of dye perfusion in the first seconds in malignant tissue are similar to those in the first few seconds in benign tumor tissue. FIG. 2C shows that at 30 seconds the malignant tissue is even more intense by comparison to the normal tissue. FIG. 2D (1 minute after dye injection) and 2E (10 minutes after dye injection) show that dye is retained significantly longer in malignant tissue than in benign tumor tissue, and in some cases, continues to sequester in the malignant tumor tissue over longer periods of time.

FIG. 3A shows a gray-scale image of the tumor margin. FIG. 3B shows the margin with labels that the surgeon placed directly on the brain. The purpose of these labels was to identify where the surgeon was going to remove biopsy samples for histological analysis after difference images were acquired with the inventive device. FIG. 3C shows the difference image 1 minute after intravenous injection of dye and FIG. 3D shows the difference image 10 minutes after dye injection. These post-dye difference images reveal a number of sites that contain tumor tissue as well as areas of normal tissue. The accuracy of the optical imaging was confirmed post-operatively by analysis of the biopsies. Note that a small area on the lower right of FIG. 3D indicates a possible region of tumor tissue that would not have been biopsied by the surgeon.

FIG. 4D shows the area of interest 5 minutes after dye injection. Note that the dye is retained in the tumor tissue for a significant time. As shown in FIGS. 1A–1F, FIGS. 2A–2E and FIGS. 3A–3D this dynamic trait is characteristic of a non-benign tumor.

FIG. 5A is a gray-scale image of the cranial surface of a rat. The sagittal suture runs down the center of the image. Tumor cells had been injected into the left side some days earlier so that this animal had developed a glioma on the left hemisphere of its brain. The right hemisphere was normal. Box 1 lies over the suspected region of brain tumor, while box 2 lies over normal tissue. FIG. 5B is a difference image 1 second after indocyanine green dye had been intravenously injected into the animal. The region containing tumor tissue became immediately visible through the intact cranium. FIG. 5C shows that the dye can be seen to profuse through both normal and tumor tissue 5 seconds after dye injection. FIG. 5D shows that 1 minute after dye injection, the dye had cleared from the normal tissue, but was still retained in the tumor region. The concentration of dye in the center of this difference image was due to dye circulating in the sagittal sinus.

FIG. 7A shows a gray-scale image of the area of interest. Box 1 overlays the tumor, Box 2 overlays the tumor-surround, and Box 3 overlays normal tissue. FIG. 7B shows the difference image of the area of interest 1 second after 1 mg/kg of indocyanine green had been intravenously injected into the animal. During this initial time, the tumor tissue was the first to show a measurable optical change, indicating that the uptake of dye occurs first in the tumor tissue. The gray-scale bar indicates the relative magnitude of the optical changes in the sequence of difference images. FIGS. 7C and 7D show difference images of the area of interest 4 seconds and 30 seconds, respectively, after dye injection. At these intermediate stages, dye appears to collect in both normal and tumor tissue. FIGS. 7E and 7F show difference images of the area of interest 1 minute and 5 minutes, respectively, after injection of dye. At these later times, dye still remained in the tumor tissue even though it was being cleared from normal tissue.

FIG. 9A shows a higher magnification image of the left hemisphere tumor margin of the animal after the tumor has been resected. Boxes 1 overlay areas that contain small traces of residual tumor cells, and boxes 2 overlay areas containing only normal tissue. The gray-scale bar indicates the magnitude of optical change in the difference images. FIGS. 9B, 9C, and 9D show difference images of the tumor margin 4, 30, and 60 seconds, respectively, after intravenous dye injection. Minute biopsies were taken from areas that showed preferred dye containment and from areas from which the dye cleared rapidly. These biopsies were analyzed blindly and later correlated to the location from which they were taken. Those biopsies taken from areas which cleared dye were shown to contain only normal cells, whereas biopsies taken from areas which sequestered dye were shown to contain tumor cells. Extremely small islands of residual tumor can thus be mapped within tumor margins.

DETAILED DESCRIPTION OF THE INVENTION

Figure 1A:
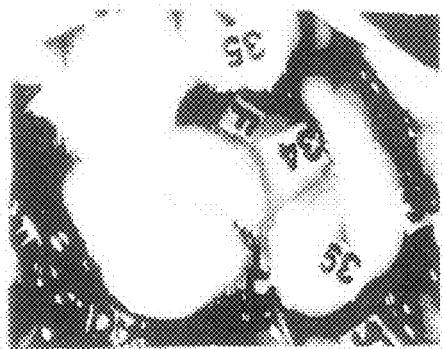
FIGS. 1A–1F illustrate identification of low grade human central nervous system (CNS) tumor tissue using the methods and apparatus of the present invention. This series of images is from a patient having a low grade CNS tumor (astrocytoma, grade 1). Tumors of this type and grade are notoriously difficult to distinguish from normal tissue once surgical removal of the tumor has begun.

Applicants' optical imaging methods and apparatus are described in greater detail below with reference to certain preferred embodiments. Certain aspects of the optical imaging techniques have been described in even greater detail in the patents incorporated herein by reference. The detailed descriptions of certain preferred embodiments are not intended to limit the scope of the applicants' invention as described herein and set forth in the appended claims.

Definitions

The following terms, as used in this specification and the appended claims, have the meanings indicated:

Area of Interest is an area of tissue that comprises the subject of acquired data sets. In a preferred embodiment, the area of interest is suspected of containing one or more sites of tumor tissue. The area of interest may, for example, be exposed tissue, tissue that underlies or is adjacent exposed tissue, or tissue cultured in vitro.

Arithmetic Logic Unit (ALU) is a component that is capable of performing a variety of processing (e.g., mathematical and logic) operations (e.g., sum, difference, comparison, exclusive or multiply by a constant, etc.) on a data set.

Control Data is data representing one or more optical properties of the area of interest during a "normal" or a predetermined period, such as prior to administration of a dye. The control data set establishes a "background" level of optical properties for comparison with a subsequently acquired data set.

Charge Coupled Device (CCD) is a type of optical detector that utilizes a photo-sensitive silicon chip in place of a pickup tube in a video camera.

Comparison Data is data acquired by comparing subsequent data or data acquired at a particular time, with control data, such as by adding, subtracting, or the like. The comparison data set is used to identify and/or locate areas of tumor versus non-tumor tissue.

Electromagnetic Radiation (emr) means energy having a wavelength of from about 450 to about 2500 nm. Emr illumination suitable for use in the optical imaging methods described herein is in the visible and infrared regions.

Frame is a digitized array of pixels.

Frame Buffer is a component that provides storage of a frame, such as a control image, a subsequent image or a comparison image.

Geometric Transformations can be used to modify spatial relationships between data points in a data set, such as pixels in an image. Geometric transformations are often called "rubber sheet transformations" because they can be viewed as the process of "printing" data, such as an image, on a sheet of rubber and stretching the sheet according to a predefined set of rules. As applied to video imaging, subsequent images can be viewed as having been distorted due to movement and it is desirable to "warp" these images so that they are spatially aligned with the control images. Geometric transformations are distinguished from "point transformations" in that point transformations modify a pixel's value in an image based solely upon that pixel's value and/or location, and no other pixel values are involved in the transformation. Geometric transformations are described in the publication *Digital Image Processing*, Gonzalez and Wintz, Addison-Wesley Publishing Co., Reading, 1987.

Image is a frame or composition of frames representing one or more optical properties of an area of interest.

Optical Properties relate to various properties detectable in the useful range of emr (450–2500 nm) including but not limited to scattering (Rayleigh scattering, reflection/retraction, diffraction), absorption and extinction, birefringence, refractive index, Kerr effect and the like.

Optical Detector is a device capable of detecting one or more desired optical properties of an area of interest. Suitable optical detectors include any type of photon detector, such as photodiodes, photomultiplier tubes, cameras, video cameras, CCD cameras, and the like.

Optical Imaging refers to the acquisition, comparison, processing and display of data representative of one or more optical properties of an area of interest. Optical imaging may involve acquisition processing and display of data in the form of images, but need not.

Pixels are the individual units of an image in each frame of a digitized signal. The intensity of each pixel is linearly proportional to the intensity of illumination before signal manipulation and corresponds to the amount of emr (photons) being scattered from a particular area of tissue corresponding to that particular pixel. An image pixel is the smallest unit of a digital image and its output intensity can be any value. A CCD pixel is the smallest detecting element on a CCD chip and its analog output is linearly proportional to the number of photons it detects.

Subsequent Data is data representing one or more optical properties of an area of interest during a monitoring period or subsequent to administration of a dye.

Tumor Margin is the area where the surgeon has resected a tumor.

Apparatus

The inventive methods employ an apparatus comprising a source of high intensity emr, an optical detector for acquiring data representative of one or more optical properties of the area of interest, such as video signals, and image processing capability. The apparatus may be constructed as an integrated unit, or it may be used as a collection of components. The apparatus will be briefly described with reference to the schematic diagram, illustrated in FIG. 11, and various components and features will then be described in greater detail.

Figure 11:
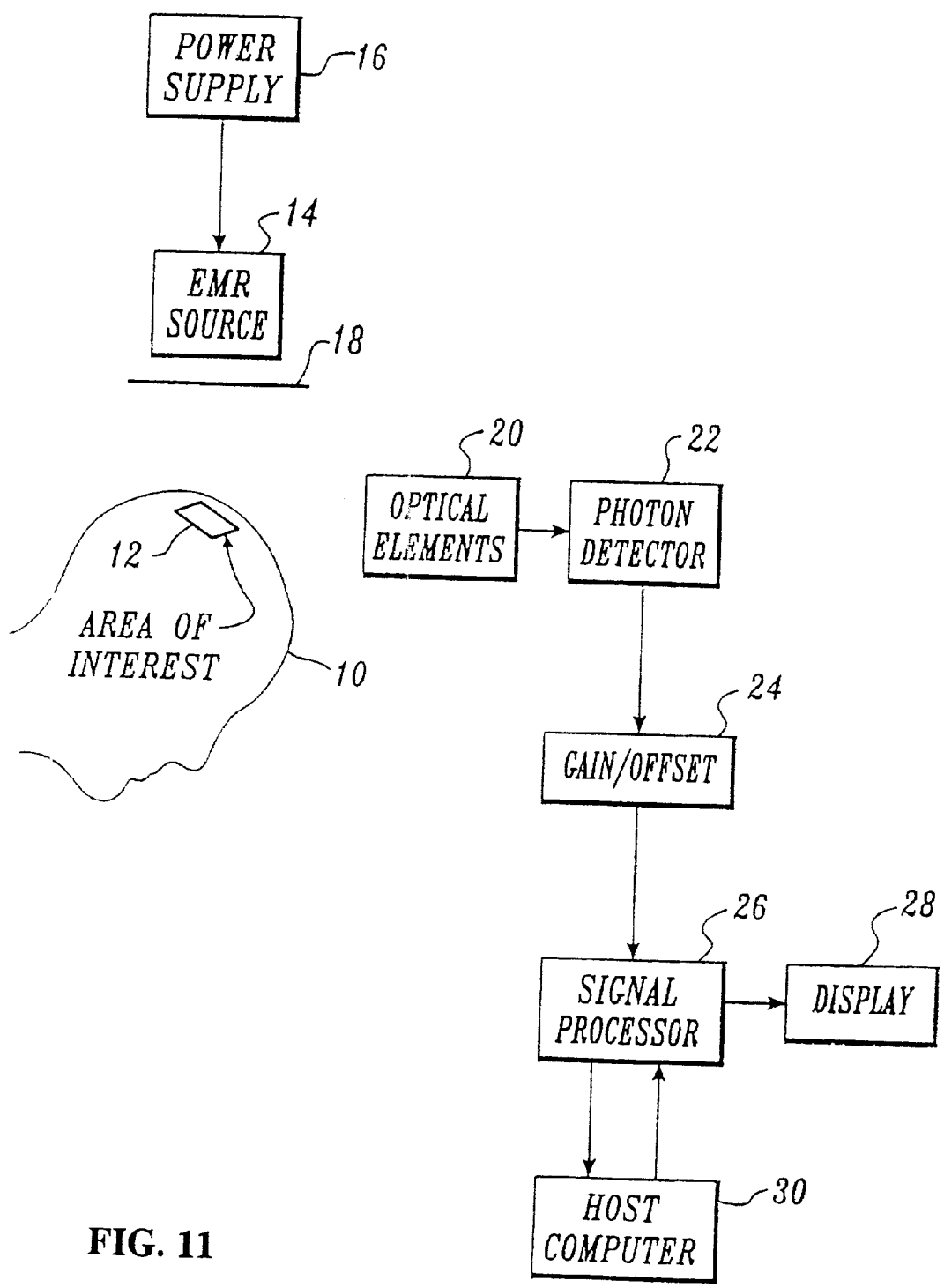
FIG. 11 is a simplified schematic diagram illustrating an apparatus of the present invention.

FIG. 11 illustrates a human patient 10 whose neuronal tissue represents area of interest 12. As is described in greater detail below, area of interest 12 may be fully or partially exposed, or imaging may be conducted through bone and/or dura with proper selection of emr wavelengths. During optical imaging, area of interest 12 is uniformly illuminated by emr source 14 powered by regulated power supply 16. Emr is preferably directed through an optical filter 18 prior to contacting area of interest 12.

During optical imaging, a light gathering optical element 20, such as a camera lens, endoscope, optical fibers and photon detector 22 or the like are placed to detect optical properties of area of interest 12. Signals representative of optical properties are processed, if desired, in a gain, offset component 24 and then conveyed to analog-to-digital (A/D) and digital signal processing hardware 26. Data representing optical properties and particularly changes in optical properties, are displayed on display device 28. The optical detection, display and processing components are controlled by host computer 30.

An emr source is used for illuminating the area of interest during acquisition of data representing one or more optical properties. The emr source may be utilized to illuminate an area of interest directly, as when tissue is exposed during or in connection with surgery, or it may be utilized to illuminate an area of interest indirectly through adjacent or overlying tissue such as bone, dura, skin, muscle and the like.

The emr source employed in the present invention is preferably a high intensity, broad spectrum emr source, such as a tungsten-halogen lamp, laser, light emitting diode, or the like. Cutoff filters to selectively pass all wavelengths above or below a selected wavelength may be employed. A preferred cutoff filter excludes all wavelengths below about 695 nrm. Instead of using cutoff filters, administration of a first dye prior to administration of a second, different dye can act as a tissue filter of emr to provide a filter in the area of interest. In this instance, it is desirable to utilize a dye that remains with tumor or normal tissue for a prolonged period of time.

Preferred emr wavelengths for imaging include, for example, wavelengths of from about 450 nm to about 2500 nm, and most preferably, wavelengths of the near infrared spectrum of from about 700 nm to about 2500 nm. Generally, longer wavelengths (e.g., approximately 800 nm) are employed to image deeper areas of tissue. Moreover, if a difference image is created between the image seen with 500 nm emr and the image seen with 700 nm emr, the difference image will show an optical slice of tissue. Selected wavelengths of emr may also be used, for example, when various types of contrast enhancing agents are administered.

The emr source may be directed to the area of interest by a fiber optic means. One preferred arrangement provides emr through fiber optic strands using a beam splitter controlled by a D.C. regulated power supply (Lambda, Inc.).

The area of interest must be evenly illuminated to effectively adjust the signal over a full dynamic range, as described below. Nonuniformity of illumination is generally caused by fluctuations of the illumination source and intensity variations resulting from the three-dimensional nature of the tissue surface. More uniform illumination can be provided over the area of interest, for example, by using diffuse lighting, mounting a wavelength cutoff filter in front of the optical detector and/or emr source, or combinations thereof. Fluctuation of the illumination source itself is preferably addressed by using a light feedback mechanism to regulate the power supply of the illumination source. In addition, a sterile, optically transparent plate may contact and cover the area of interest to provide a flatter, more even contour. The plate also diminishes tissue movement. Fluctuations in illumination can be compensated for by using image processing algorithms, including placing a constant shade gray image marker point at the area of interest as a control point.

The apparatus also comprises an optical detector for acquiring a signal representative of one or more optical properties of the area of interest. Any photon detector may be employed as an optical detector. Specialized detectors suited for detecting selected optical properties may be employed. One preferred optical detector for acquiring data in the format of an analog video signal is a charge coupled device (CCD) video camera which produces an output video signal at 30 Hz having, for example, 512 horizontal lines per frame using standard RS 170 convention. One suitable device is a CCD-72 Solid State Camera (Dage-MTI Inc., Michigan City Ind.). Another suitable device is a COHU 6510 CCD Monochrome Camera with a COHU 6500 electronic control box (COHU Electronics, San Diego, Calif.). In some cameras, the analog signal is digitized 8-bits deep on an ADI board (analog-to-digital board). The CCD may be cooled, if necessary, to reduce thermal noise.

The optical imaging methods of the present invention may also usefully employ non-continuous illumination and detection techniques. For example, short pulse (time domain), pulsed time, and amplitude modulated (frequency domain) illumination sources may be used in conjunction with suitable detectors (See, Yodh, A., and Chance, B. *Physics Today,* March, 1995). Frequency domain illumination sources typically comprise an array of multiple source elements, such as laser diodes, with each element modulated at 180° out of phase with respect to adjacent elements (see, Chance, B. et al., (1993) *Proc. Natl. Acad. Sci. USA,* 90, 3423–3427). Two-dimensional arrays, comprising four or more elements in two orthogonal planes, can be employed to obtain two-dimensional localization information. Such techniques are described in U.S. Pat. Nos. 4,972,331 and 5,187,672 which are hereby incorporated by reference.

Time-of-flight and absorbance techniques (Benaron, D. A. and Stevenson, D. K. (1993) *Science,* 259, 1463–1466) may also be usefully employed in the present invention. In yet another embodiment of the present invention, a scanning laser beam may be used in conjunction with a suitable detector, such as a photomultiplier tube, to obtain high resolution images of an area of interest.

Illumination with a part of the infrared spectrum allows for imaging intrinsic signals through tissue overlying or adjacent the area of interest, such as dura and skull. One exemplary infrared emr source suitable for imaging through tissue overlying or adjacent the area of interest is a Tunable IR Diode Laser from Laser Photonics, Orlando, Fla. When using this range of far infrared wavelengths, the optical detector is preferably provided as an infrared (IR) detector. IR detectors are made from materials such as indium arsenide, germanium and mercury cadmium telluride, and are generally cryogenically cooled to enhance their sensitivity to small changes in infrared radiation. One example of an IR imaging system which may be usefully employed in the present invention is an IRC-64 infrared camera (Cincinnati Electronics, Mason Ohio).

Image (data) processing is an important feature of the optical imaging techniques and apparatus of the present invention. In use, for example, a CCD apparatus is preferably adjusted (at the level of the analog signal and before digitizing) to amplify the signal and spread the signal across the full possible dynamic range, thereby maximizing the sensitivity of the apparatus. Specific methods for detecting optical signals with sensitivity across a full dynamic range are described in detail in the patents incorporated herein by reference. Means for performing a histogram stretch of the difference frames (e.g., Histogram/Feature Extractor HF 151-1-V module, Imaging Technology, Woburn Mass.) may be provided, for example, to enhance each difference image across its dynamic range. Exemplary linear histogram stretches are described in Green, *Digital Image Processing:*

*A Systems Approach*, Van Nostrand Reinhold, N.Y., 1983. A histogram stretch takes the brightest pixel, or one with the highest value in the comparison image, and assigns it the maximum value. The lowest pixel value is assigned the minimum value, and every other value in between is assigned a linear value (for a linear histogram stretch) or a logarithmic value (for a log histogram stretch) between the maximum and minimum values. This allows the comparison image to take advantage of the full dynamic range and provide a high contrast image that clearly identifies areas of tumor tissue.

Noise (such as 60 Hz noise from A.C. power lines) is filtered out in the control box by an analog filter. Additional adjustments may further enhance, amplify and condition the analog signal from a CCD detector. One means for adjusting the input analog signal is to digitize this signal at video speed (30 Hz), and view the area of interest as a digitized image that is subsequently converted back to analog format.

It is important that data, such as consecutive images of a particular area of interest, be aligned so that data corresponding to the same spatial location can be compared. If an averaged control image and a subsequent image are misaligned prior to comparison, artifacts will be present and the resulting comparison image will be more like a gradient image that amplifies noise and edge information. Image misalignment can be caused by patient motion, heartbeat and respiration. Large patient movements may require a new orientation of the camera and acquisition of a new averaged control image. It is possible, however, to compensate for small tissue movements by either mechanical or computational means, or a combination of both.

One way to reduce relative movement of the optical detector and the area of interest is to rigidly secure the optical detector, and possibly the emr source, to the skeletal frame of the patient, such as by posts mounted on the cranium. The optical detector and emr source may also be provided as an integral unit to reduce relative motion. Other means for maintaining the optical detector and the illumination source in a constant orientation with respect to the area of interest may also be employed.

Real-time motion compensation and geometric transformations may be used to align corresponding data. Simple mechanical translation of data or more complex (and generally more accurate) geometric transformation techniques can be implemented, depending upon the input data collection rate and amount and type of data processing. For many types of images, it is possible to compensate by a geometrical compensation which transforms the image by translation in the x-y plane. In order for an algorithm such as this to be feasible, it must be computationally efficient (preferably implementable in integer arithmetic), memory efficient, and robust with respect to changes in ambient light.

For example, functional control points can be placed in the area of interest and triangulation-type algorithms used to compensate for movements of these control points. Control points can be placed directly in the area of interest, such as directly on the cortical surface. Goshtasby ("Piecewise Linear Mapping Functions for Image Registration" in *Pattern Recognition* vol. 19 pp 459–66, 1986) describes a method whereby an image is divided into triangular regions using control points. A separate geometrical transformation is applied to each triangular region to spatially register each control point to a corresponding triangular region in a control image.

"Image warping" techniques may be employed whereby each subsequent image is registered geometrically to the averaged control image to compensate for movement. Image warping techniques described in, for example, Wolberg, "Digital Image Warping" IEEE Computer Society Press, Los Alimitos, Calif. 1990, may be used. Image warping techniques can further indicate when movement has become too great for effective compensation and a new averaged control image must be acquired.

The data processing function is generally operated and controlled by a host computer. The host computer may comprise any general computer (such as an IBM PC type with an Intel 386, 486 Pentium or similar microprocessor or Sun SPARC) that is interfaced with the emr source and/or optical detector and directs data flow, computations, image acquisition and the like. Thus, the host computer controls acquisition and processing of data and provides a user interface.

According to a preferred embodiment, the host computer comprises a single-board embedded computer with a VME64 interface, or a standard (IEEE 1014-1987) VME interface, depending upon bus band width considerations. Host computer boards which may be employed in the present invention include, for example, Force SPARC/CPU-2E and HP9000 Model 7471. The user interface can be, for example, a Unix/X-Window environment. The image processing board can be, for example, based upon Texas Instruments' MVP and other chips to provide real-time image averaging, registration and other processing necessary to produce high quality difference images for intraoperative viewing. This board will also drive a 120×1024 RGB display to show a sequence of difference images over time with pseudo-color mapping to highlight tumor tissue. Preferably, a second monitor is used for the host computer to increase the overall screen real estate and smooth the user interface. The processing board (fully programmable) can support a VME64 master interface to control data transactions with the other boards. Lastly, a peripheral control board can provide electrical interfaces to control mechanical interfaces from the host computer. Such mechanical interfaces can include, for example, the light source and optical detector control box.

A real-time data acquisition and display system, for example, may comprise four boards for acquisition, image processing, peripheral control and host computer. A minimal configuration with reduced processing capabilities may comprise just the acquisition and host computer boards. The acquisition board comprises circuitry to perform real-time averaging of incoming video frames and allow readout of averaged frames at a maximum rate bus. A VME bus is preferred because of its high peak bandwidth and compatibility with a multitude of existing VME products. The acquisition board should also support many different types of optical detectors via a variable scan interface. A daughter board may support the interfacing needs of many different types of optical detectors and supply variable scan signals to the acquisition motherboard. Preferably, the unit comprises a daughter board interfacing to an RS-170A video signal to support a wide base of cameras. Other camera types, such as slow scan cameras with a higher spatial/contrast resolution and/or better signal to noise ratio, can be developed and incorporated in the inventive device, as well as improved daughter boards to accommodate such improved cameras.

According to a preferred embodiment, data, such as analog video signals, are continuously processed using, for example, an image analyzer (e.g., Series 151 Image Processor, Imaging Technology, Inc., Woburn Mass.). An image analyzer can receive and digitize an analog video signal with an analog to digital interface and perform such a function at a frame speed of about $\frac{1}{30}$th of a second (e.g., 30 Hz or "video speed"). Processing the signal involves first digitizing the signal into a series of pixels or small squares assigned a value (in a binary system) dependent upon the number of photons (i.e., quantity of emr) being detected from the part of the area of interest assigned to that pixel. For example, in a standard 512×512 image from a CCD camera, there would be 262,144 pixels per image. In an 8 bit system, each pixel is represented by 8 bits corresponding to one of 256 levels of gray.

The signal processing means preferably includes a programmable look-up table (e.g., CM150-LUT16, Imaging Technology, Inc., Woburn, Mass.) initialized with values for converting gray coded pixel values, representative of a black and white image, to color coded values based upon the intensity of each gray coded value. This can provide image enhancement via an image stretch. An image stretch is a technique whereby the highest and lowest pixel intensity values used to represent each of the pixels in a digital image frame are determined over a region of the image frame which is to be stretched. Stretching a selected region over a larger range of values permits, for example, easier identification and removal of relatively high, spurious values due to noise (e.g., glare).

The processing means may further include a plurality of frame buffers having frame storage areas for storing frames of digitized image data received from the analog/digital interface. The frame storage area comprises at least one megabyte of memory space, and preferably at least 8 megabytes of storage space. An additional 16-bit frame storage area is preferred as an accumulator for storing processed image frames having pixel intensities represented by more than 8 bits. The processing means preferably includes at least three frame buffers, one for storing the averaged control image, another for storing the subsequent image, and a third for storing a comparison image.

According to preferred embodiments, the processing means further comprises an arithmetic logic unit (e.g., ALU-150 Pipeline Processor) for performing arithmetical and logical functions on data located in one or more frame buffers. An ALU may, for example, provide (data) averaging in real time. A newly acquired digitized image may be sent directly to the ALU and combined with control image stored in a frame buffer. A 16 bit result can be processed through an ALU, which will divide this result by a constant (i.e., the total number of images). The output from the ALU may be stored in a frame buffer, further processed, or used as an input and combined with another image.

The comparison (e.g., difference) data is, preferably, further processed to smooth out the image and remove high frequency noise. For example, a lowpass spatial filter can block high spatial frequencies and/or low spatial frequencies to remove high frequency noises at either end of the dynamic range. This provides a smoothed-out processed difference image (in digital format). The digitally processed difference image can be color-coded by assigning a spectrum of colors to differing shades of gray. This image is then converted back to an analog image (by an ADI board) and displayed for a real time visualization of differences between an averaged control image and subsequent images. Moreover, the processed difference image can be superimposed over the analog image to display specific tissue sites where a dye or contrast enhancing agent may have a faster uptake.

Processing speed may be enhanced by adding a real time modular processor or faster CPU chip to the image processor. One example of a real time modular processor which may be employed in the present invention is a 150 RTMP-150 Real Time Modular Processor (Imaging Technology, Woburn, Mass.).

The processing means may further include an optical disk for storing digital data, a printer for providing a hard copy of the digital and/or analog data and a display, such as a video monitor to permit the physician to continuously monitor the comparison data output.

A single chassis may house all of the modules necessary to provide optical imaging according to the present invention. The necessary components, whether or to whatever degree integrated, may be installed on a rack that is easily transportable within and between operating and hospital rooms along with display monitors and peripheral input and output devices.

Imaging Methods

The method for imaging a solid tumor involves periodically administering a dye by bolus injection into vasculature (e.g., artery or vein) perfusing the suspected tumor site in the area of interest. Preferably, the dye has a relatively short half life (e.g., less than five minutes) and is rapidly cleared to allow for repeated administration. An optical detector, such as a video CCD, is focused upon the suspected solid tumor site (area of interest) and high intensity emr containing a wavelength which interacts with the dye illuminates the site. The form of interaction between the emr and the dye will depend on the specific dye being used. For example, in the case of a fluorescent dye, the preferred wavelength of emr is one which excites the dye, thereby causing fluorescence. However with some dyes, such as indocyanine green, the preferred wavelength of emr is one which is absorbed by the dye. Just prior to administration of the dye, the first averaged image, or control image is taken, digitized and stored in a frame buffer. The dye is injected quickly and rapidly as a bolus. Subsequent image frames are taken and stored and subtractively compared to produce comparison, or difference, images (e.g., one or two per second) using the inventive processing means.

Initial visualization of the dye will appear in the comparison image first in tumor tissue because the dye perfuses more rapidly into tumor tissue than non-tumor tissue. Solid tumor margins will be the first images to appear in the comparison image as darkened lines outlining a solid tumor mass. This comparison image can be frozen and stored to allow the surgeon to study the tumor image and identify tumor margins in real time during an operation. The dye will remain for a longer period of time in tumor tissue compared to normal tissue. Therefore, after there is general appearance of the dye throughout the area of interest in both normal tissue and tumor tissue, the dye clearance in tumor tissue will be delayed, allowing another opportunity to visualize tumor margins by dye presence in tumor tissue but not in normal tissue.

The more aggressive or malignant the tumor (higher tumor grade), the longer the dye remains in the tumor tissue. For lower grade or more benign tumors, the dye remains in tumor tissue for 45 sec to 2 min, whereas the dye can remain in more malignant tumors for up to 10 minutes.

In an alternative embodiment of the present invention, solid tumor tissue may be distinguished from non-tumor tissue and characterized by administering a dye to the area of interest, illuminating the area of interest with emr containing a wavelength that interacts with the dye, and detecting differences in one or more optical properties between the tumor tissue and non-tumor tissue.

The inventive method is superior to established tumor imaging techniques, such as MRI, because it can optically image and distinguish low grade tumors that cannot be distinguished with current MRI techniques, and updated images are continually available during a surgical procedure by readministering the dye. The dye can be administered on multiple occasions during a surgical procedure after resection has begun to look at resected walls for residual tumor tissue. For CNS tumors, MRI techniques can only image advanced stage tumors that have compromised the blood brain barrier. The present optical imaging method, by contrast, can image even low grade tumors that have not yet compromised the blood brain barrier.

The dye can be any emr-absorbing or fluorescent dye that is safe for in vivo administration, and has a short half-life when administered intravenously or intraarterially. Further, during surgical resection of a solid tumor, it is important that the dye be rapidly cleared from the area of interest so that dye can be administered repeatedly to image residual tumor tissue. Dyes suitable for use with the present invention include indocyanines, fluoresceins, hematoporphyrins, fluoresdamine and other dyes used for photodynamic treatment of tumor tissue, such as those available from Quadra Logic Technologies, Inc. (Vancouver, B.C.). Specific examples of dyes which may be usefully employed with the present invention include indocyanine green, PHOTOFRIN® a hematoporphyrin dye, NPe$_6$, BPD, Evans Blue, BIODIPY® dyes, a series of fluorophores; (available from Molecular Probes, Inc., Eugene, Oreg.) and combinations thereof.

Without being bound by theory, the dynamic differences in dye perfusion through normal brain tissue surrounding and tumor tissue could be accounted for by any one or a combination of the following four reasons: (1) greater extravasation of the dye through leaky tumor capillaries; (2) more rapid uptake of the dye by tumor tissue; (3) slower transit times through tumor tissue; and (4) preferential uptake of the dye by tumor cells.

Microvasculature in the rat glioma model has been examined and compared to normal cortex. Blood flow in tumor tissue is slower and more variable than in normal tissue. These differences have been attributed to tumor location, degree of infiltration, and necrosis. In other studies using cultured spheroids of C6 astroglial cells transplanted into rat brain, blood flow was slower in viable tumor than in normal rat brain. Microvessel volume fraction was equivalent between tumor and normal brain. However, since only about 50% of the tumor was actively perfused, the surface area of perfused microvessels in the tumor was one-half that of the normal brain. These changes could account for a slower flow of dye through the tumor compared to normal brain and also lead to more rapid clearance by the normal brain in contrast to the tumor.

The permeability of tumor capillaries is much higher than that of normal brain. This leakiness of tumor capillaries leads to extravasation of larger particles is resulting in edema and an increase in interstitial pressure surrounding tumor microvessels. Since tumor microvessels do not contain normal arteriole smooth muscle, they also have no local control of pressure gradients. This leads to a stasis of flow in tumor tissue. The overall effect on dye perfusion is longer transit times than in normal brain. Such reasoning supports the dynamic changes in optical properties in tumor and normal tissue that are seen during dye perfusion. There is nearly equivalent uptake, but a much slower transit time in tumor tissue, resulting in prolonged increases in optical properties compared to normal tissue. Also, tissue surrounding the tumor is expected to have increased interstitial pressures but without leaky capillaries and other microvasculature changes, thereby accounting for the fact that tumor margin tissue has an intermediate duration of optical changes.

Yet another aspect of the inventive method involves using an emr absorbing or fluorescent dye conjugated to a targeting molecule, such as an antibody, or more particularly, a monoclonal antibody or fragment thereof specific for an antigen surface marker of a tumor cell. The area of interest is illuminated with emr containing excitation wavelengths of the fluorescent dye but not emission wavelengths. This can be accomplished by use of a cutoff filter over the emr source. Preferably, the optical detector is coupled to an image intensifier or micro channel plate (e.g., KS-1381 Video Scope International, Wash D.C.) to increase the sensitivity of the system by several orders of magnitude and allow for visualization of cells having fluorescent dyes attached thereto. Examples of fluorescent dyes that can be conjugated to a targeting molecule include, for example, Cascade Blue, Texas Red and Lucifer Yellow CH from Molecular Probes, Eugene, Oreg.

The methods and apparatus described herein for optical imaging of tumor tissue can operate outside of a surgical procedure setting. More specifically, it is possible to optically image tissue through intact skin and bone. In some areas of the body, longer wavelength visible light and near infrared emr can easily pass through tissue, such as breast tissue. With dye injection, areas of increased vascularity, such as tumor tissue can be identified. The optical imaging techniques of the present invention can therefore be used, for example, to screen for tumors in breast and other tissue.

EXAMPLE 1

This example illustrates optical imaging of a low grade CNS tumor (astrocytoma, grade 1) using the methods and apparatus of the present invention. A MRI scan was conducted before the operation. However, tumors of this type and grade are notoriously difficult to distinguish from normal tissue once the surgical removal of the tumor has begun.

All imaging procedures reported in this and in the following examples were reviewed and approved by the University of Washington Human Subjects Review Committee. All patients signed an informed consent form for both the surgery and the imaging experiments.

The imaging procedure used in Examples 1–4 was as follows. The area of interest was evenly illuminated by a fiber optic light source with the radiation passing through a beam splitter, controlled by a D.C. regulated power supply (Lambda, Inc.) and passed through a 695 nm longpass filter. Images were acquired with a CCD camera (COHU 6500) fitted to the operating microscope with a specially modified cineadaptor. The cortex was stabilized with a glass footplate. Images were acquired at 30 Hz and digitized at 8 bits (512×480 pixels, using an Imaging Technology, Inc. Series 151 system, Woburn, Mass.). Geometrical transformations were applied to images to compensate for small amounts of patient motion (Wohlberg, *Digital Imaging Warping*, I.E.E.E. Computer Society, Los Alamitos, Calif., 1988). Subtraction of images collected following dye administration from those collected during a control state with subsequent division by the control image resulted in percentage difference maps. Raw data (i.e., no digital enhancement) were used for determining the average optical change in specified regions (average size box was 30×30 pixels or 150–250 um$^2$). For pseudocolor images, a linear low pass filter removed high frequency noise and linear histogram transformations were applied. Noise was defined as the standard deviation of fluctuations in sequentially acquired control images as 0.003–0.009.

Figure 1D:
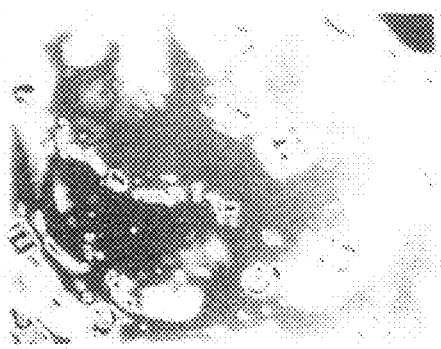
Figure 1B:
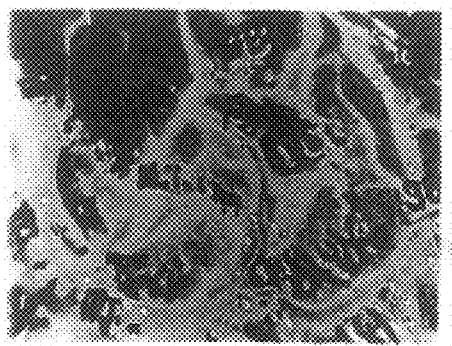
Figure 1E:
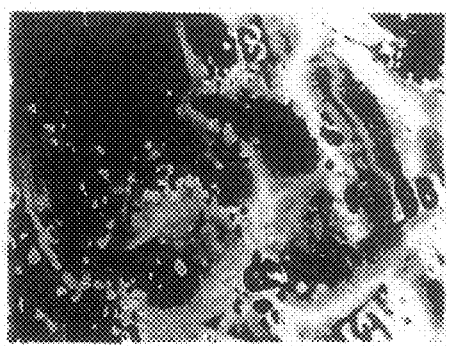
Figure 1C:
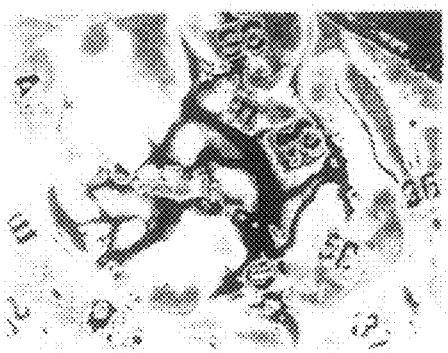
Figure 1F:
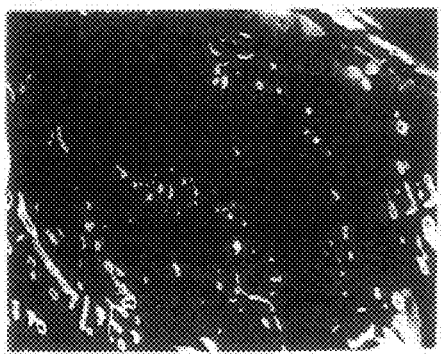

An averaged control image was obtained of the particular cortical surface area of interest. FIG. 1A is a gray-scale image of the area of interest prior to dye administration. The lettered labels placed upon the brain by the surgeon overlay the tumor as identified intraoperatively by ultrasound. Indocyanine green dye (1 mg/kg) was administered into a peripheral intravenous catheter as a bolus at time 0. FIG. 1B shows a difference image taken approximately 15 seconds after intravenous injection of dye. FIG. 1C shows the difference image about 30 seconds after dye administration. The area of the tumor tissue showed the first tissue staining. FIG. 1D shows that with this low grade tumor, all tissue (both normal and abnormal) showed staining at 45 sec after dye administration. FIG. 1E is an image of the area of interest one minute after dye administration and FIG. 1F is the image five minutes after dye administration showing complete clearance in this low grade tumor. In all the examples presented herein demonstrating optical imaging in humans, each image covers an area of approximately 4 cm×4 cm.

These data show that indocyanine green enters low grade tumor tissue faster than normal brain tissue, and may take longer to be cleared from benign tumor tissue than normal tissue. Therefore, it is possible to image even low grade tumors with this apparatus. Furthermore, it is possible to distinguish low grade tumor tissue from surrounding normal tissue intraoperatively. Subsequent pathology of this tumor tissue established it as a low grade glioma.

EXAMPLE 2

Figure 2A:
FIGS. 2A–2E illustrate identification of a malignant human CNS tumor using the methods and apparatus of the present invention. The series of images in this Figure are from the cortex of a patient with a malignant CNS tumor (glioblastoma; astrocytoma, Grade IV).
Figure 2D:
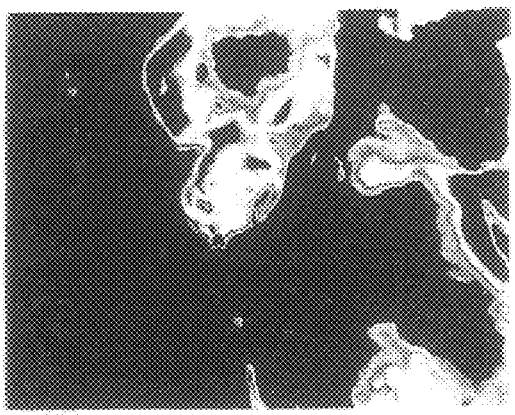
Figure 2B:
Figure 2E:
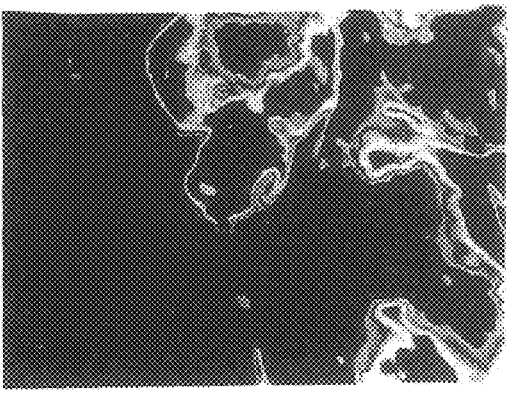
Figure 2C:
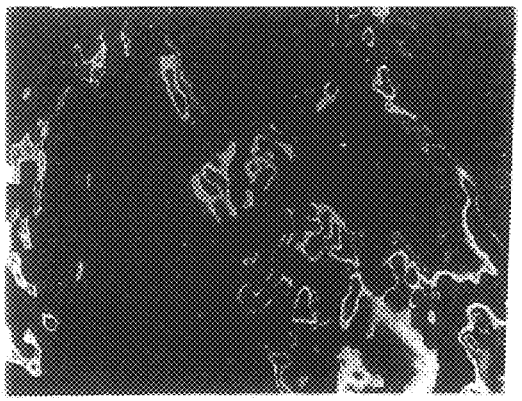

This example illustrates optical imaging of a highly malignant CNS tumor (glioblastoma; astrocytoma, grade IV). FIG. 2A shows a gray-scale image in which malignant brain tumor tissue was densest in the center and to the right but that the tissue elsewhere was mostly normal. This illustrates that the optical imaging methods and apparatus of the present invention may be employed to distinguish between tumor and non-tumor tissue without the use of contrast enhancing agents, following optimization of the gain and offset on the photodetector. However, a higher resolution is obtained with the use of contrast enhancing agents. The imaging data were confirmed by pathology slides and flow cytometry data available one week after surgery. FIG. 2B is the difference image at 15 seconds after intravenous injection of indocyanine green, showing that the dynamics of dye perfusion in the first seconds in malignant tissue are similar to those in the first few seconds in benign tumor tissue. FIG. 2C shows that at 30 seconds the dye uptake in malignant tissue is even more intense by comparison to the normal tissue. FIG. 2D (1 minute after dye injection) and 2E (10 minutes after dye injection) show that dye is retained significantly longer in malignant tissue than in benign tumor tissue and, in some cases, continues to sequester in the malignant tumor tissue over longer periods of time. Therefore, using the apparatus and methods of the present invention, it is possible to identify malignant tumor tissue, distinguish intraoperatively between normal and malignant tumor tissue, and to distinguish between the various grades of tumor (e.g., normal vs. benign vs. malignant). Thus, it is possible to not only image the location and margins of tumor tissue, but also to grade the tumor with more malignant tumors retaining dye for a longer period of time than lower grade tumors.

EXAMPLE 3

Figure 3A:
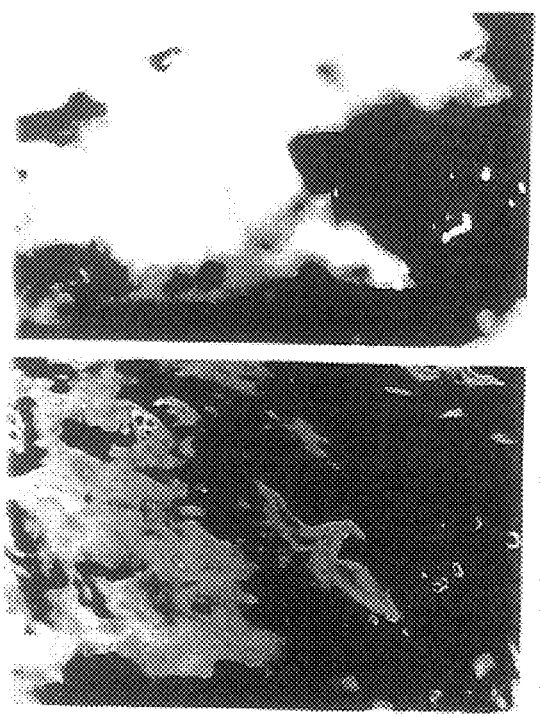
FIGS. 3A–3D show identification of small remnants of tumor tissue in the margin of a resected malignant human CNS tumor using the present invention. The images are from an area of interest where a tumor was surgically resected and biopsies were taken for multiple histological margin sampling. The area of interest was thought to be free of tumor tissue after the surgical removal of the tumor. Normally, in this size of a resection margin, only a single frozen sample would be taken for pathology analysis. For the purpose of this study, however, five biopsies were taken from the margin to aid in correlating the histology with the optical image obtained by the present invention.
Figure 3B:
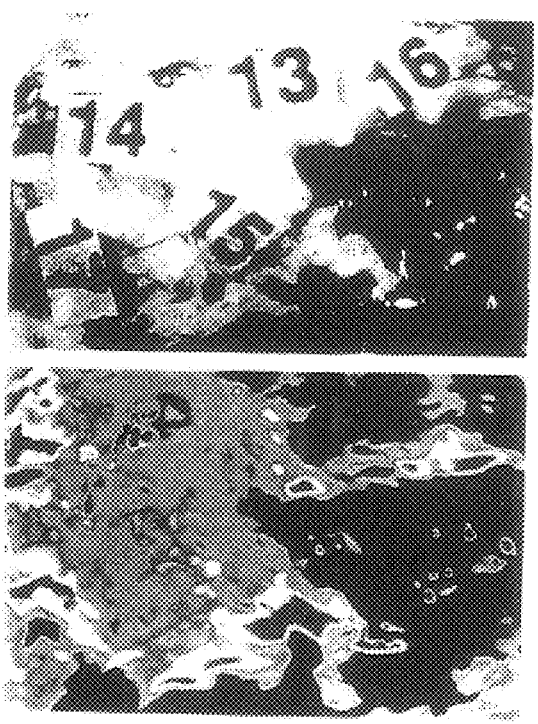
Figure 3C:
Figure 3D:
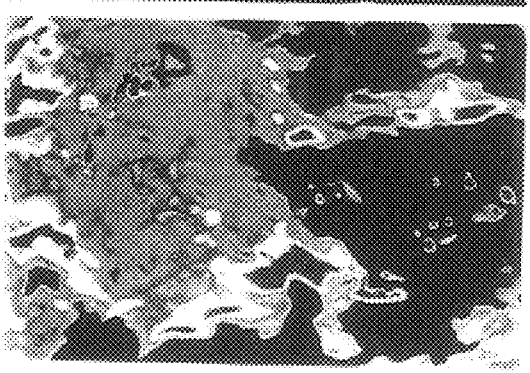

This example illustrates optical mapping of the margins of a malignant CNS tumor. FIG. 3 shows a series of images and difference images of the area of interest taken after surgical removal of the tumor and when the area was thought to be free of tumor tissue. Normally, in this size of a resection margin, only a single frozen sample would be taken for pathology analysis. For the purpose of this study, five biopsies were taken from the margin to aid in correlating the histology with the map obtained by the invention. FIG. 3A shows a gray-scale image of the tumor margin. FIG. 3B shows the margin with labels that the surgeon placed directly on the brain to identify where the surgeon was going to remove biopsy samples for histological analysis after difference images were acquired with the inventive device. FIG. 3C shows the difference image 1 minute after intravenous injection of dye and FIG. 3D shows the difference image 10 minutes after dye injection. These is post-dye difference images reveal a number of sites that contain tumor tissue as well as areas of normal tissue. The accuracy of the optical imaging was confirmed post operatively by analysis of the biopsies. Note that a small area on the lower right of FIG. 3D indicates a possible region of tumor tissue that would not have been biopsied by the surgeon. These data show that the invention is able to identify small remnants of tumor tissue in a tumor margin after resection of a tumor. In addition, the invention could act as an aid to removing biopsies from the site of a tumor margin, thereby reducing the sampling error associated with the presently used random sampling technique.

EXAMPLE 4

Figure 4A:
FIG. 4A shows the gray-scale, field of view, image of the area of interest.
Figure 4B:
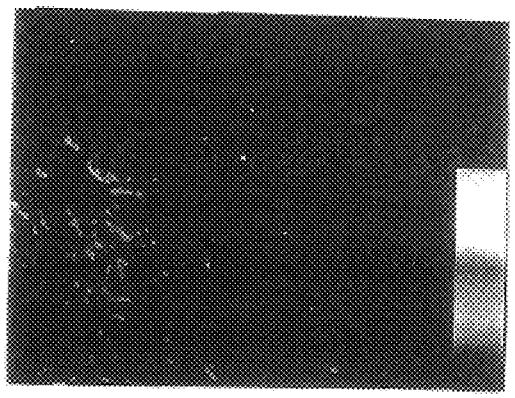
FIG. 4B shows the difference image, or control image, prior to dye injection.
Figure 4C:
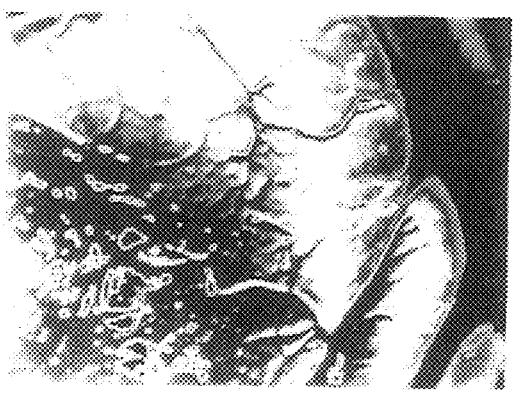
FIG. 4C shows the area of interest 1 minute after intravenous dye injection.
Figure 4D:
FIGS. 4D–4D illustrates use of the methods and apparatus of the present invention to identify and characterize tumors that do not contrast enhance with MRI imaging. Lack of contrast enhancement is usually typical of benign tumors, however a proportion of non-benign tumors are not observable with current MRI imaging techniques. The images in this Figure are from a patient whose tumor did not contrast enhance with MRI. However, optical imaging as described herein identified this tumor as non-benign. Pathology and flow cytometry data, available one week later, confirmed that this tumor was an anaplastic astrocytoma.

This example illustrates that the methods and apparatus of the present invention can be used to characterize and identify tumor tissue that does not contrast enhance with traditional MRI imaging. Lack of MRI enhancement is usually typical of benign tumors. However, a proportion of non-benign tumors are not observable with s present MRI imaging techniques. The images in FIG. 4 are from a patient whose tumor did not contrast enhance with MRI. However, optical imaging was able to identify this tumor as a non-benign type. Pathology and flow cytometry data available one week after surgery confirmed that this tumor was an anoplastic astrocytoma. FIG. 4A shows the gray-scale image of the area of interest. FIG. 4B shows the difference image prior to dye injection. FIG. 4C shows the area of interest 1 minute after intravenous dye injection, and FIG. 4D shows the area of interest 5 minutes after dye injection. Note that the dye is retained in this tissue for a significant time. As shown in FIGS. 1, 2, and 3, this dynamic trait is a characteristic of a non-benign tumor.

EXAMPLE 5

This example illustrates a series of experiments using a rat glioma model intraoperatively to investigate whether the inventive methods and device could function in an operating room setting to provide real time information to the surgeon regarding resection of all tumor tissue.

The rat glioma model is a standard predictive model and was used to delineate dye uptake, clearance and overall parameters of optical imaging that result in the best images. The advantages of this model are the ability to consistently get reproducible tumors for imaging studies and to resect tumor under an operating microscope and still find residual tumor with the inventive optical imaging. A disadvantage of this model is the more sarcoma-like appearance of the tumor and a lesser degree of vascularity compared to human gliomas.

Briefly, the rat glioma model uses an ethylnitrosourea-induced F-344 rat tumor line developed from a clonal population of a spinal malignant astrocytoma. This tumor is similar to human astrocytomas microscopically and in vivo, because both have stellate-shaped cells in the brain parenchyma and both have intracytoplasmic filaments 80–100 mm in diameter as seen by scanning electron microscopy. The glioma cells were maintained in Weymouth's medium supplemented with 10% fetal calf serum. Viable cells ($5\times10^4$) were trypsinized from a monolayer culture and implanted stereotaxically into the right cerebral hemisphere of 30 syngeneic female rats, each weighing 140–160 g. The stereotaxic coordinates for right frontal lobe implantation were 4.5 mm anterior to the frontal zero plane, 3 mm right from the midline and 6 mm deep. The rats were anesthetized for implantation. The heads were shaved and scalps opened, and a 1 mm burr hole made at the appropriate coordinates. The cells were injected through a 27 gauge needle, the needle left in place for 30 sec post injection and the hole was covered with bone wax. The scalp was sutured and the animals observed for 3–4 hrs until they returned to normal activity and feeding. The animals were used 10–14 days after tumor implantation. In this model, animals begin to show clinical symptoms from the tumor by 16–19 days, such as decreased activity and feeding, hemiparesis and eventually succumb between 19–27days from mass effects due to tumor expansion.

Fourteen animals underwent complete study, including imaging before and after resection of the tumor. The animals were anesthetized with 2% isoflurane, and the femoral vein cannulated for administration of the dye. Anesthesia was maintained with a-chloralose (50 mg/kg administered ip) and urethane (160 mg/kg administered ip). The animals were placed in a stereotaxic holder. Imaging studies were then carried out before or after removal of the cranium. The tumor typically occupied the anterior one half to two thirds of the right hemisphere exposure. The compressed brain without any tumor infiltration was defined as the tumor surround to separate it from the normal hemisphere on the contralateral side.

Following imaging of the area of interest, an operating microscope was used to attempt gross total removal of the tumor. Sites were then chosen for biopsy based on optical imaging results and later analyzed histologically. The biopsy specimens were fixed in 10% paraformaldehyde, Nissl stained and mounted. All specimens were read blindly and labeled either positive or negative for tumor. These data were correlated to the optical imaging results to identify residual tumor and statistical analysis (Chi square or student t-test) was performed to determine the significance of the results.

The following imaging apparatus was employed in Examples 5 and 6. Light was from a tungsten-halogen bulb regulated by a D.C. power supply, passed through a longpass filter (690 nm), and through a right angled prism reflected through a 50 or 100 mm objective lens onto the cortical surface. The reflected light was collected by the same objective lens and focused by a projection lens onto the surface of a CCD camera (COHU 6300). The imaging apparatus was attached to the stereotaxic frame which was rigidly fixed to a vibration isolation table. Specially designed automatic warping algorithms were designed to compensate for small amounts of movement. Images (512× 480 pixels) were acquired at 30 Hz and digitized at 8 bits (256 gray levels). Every 2 sec, a single image comprising 30 averaged frames was collected (1 sec) and then stored (1 sec).

Control images were collected prior to intravenous injection of indocyanine green dye at a dose of 1 mg/kg and then for 2 min after dye injection. The dye injection was made over a 1 sec period while the last control image was being stored. A period of 20 min was allowed between dye injections to allow optical images to return to baseline. The initial control images of each trial were subtracted from each other to insure that the baseline starting point of each trial was equivalent.

A single control image was chosen and then subtracted from each of the controls (4–6 images) and each of the post-dye injection images. The resultant image was divided by the original control image and multiplied by 100 to give a composite percentage difference for the entire sequence before and after dye injection. The optical change that occurred between separate control images were 0.2–0.7%, whereas the peak changes resulting from dye injection were in the range of 5–40%. The spatial resolution of an individual pixel in the image ranged from $13.5\times11.7$ mm$^2$ to $27\times25.4$ mm$^2$. Boxes measuring from 15–30 pixels per side were drawn on the images. The average percentage change in the individual boxes was calculated and used to demonstrate graphically the optical changes over time in the different types of tissue.

Figure 7A:
FIGS. 7A–7F show a spatial map of dynamic changes in tumor vs. non-tumor areas in a rat glioma model. These images are of the same animal as shown in FIG. 5, however the cranium has now been removed so as to expose the left hemisphere containing the glioma, and the right hemisphere containing normal tissue.
Figure 7B:
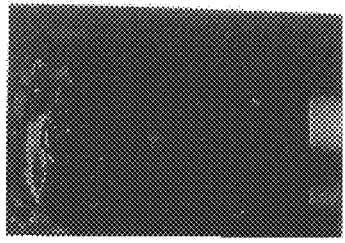
Figure 7C:
Figure 7D:
Figure 7E:
Figure 7F:

Imaging studies were performed on fourteen animals. The time course of dye perfusion through the tissue had a dynamic aspect. Optical imaging of indocyanine green dye perfusion at a dose of 1 mg/kg in 16 separate runs from a cortical surface in 9 different animals demonstrated the dynamic nature of the optical changes. In all the rat imaging examples presented herein, each image covers an area no greater than approximately 1 cm×1 cm. FIG. 7 illustrates the dynamic differences in changes in optical property due to dye absorption between tumor and non-tumor tissue. This is the same animal as shown in FIG. 5 (see, Example 6), however the cranium has now been removed so as to expose the left hemisphere containing the glioma, and the right hemisphere containing normal tissue. FIG. 7A shows a gray-scale image of the area of interest. Box 1 overlays the tumor, Box 2 overlays the tumor-surround, and Box 3 overlays normal tissue. FIG. 7B shows the difference image of the area of interest 1 second after administration of indocyanine green. During this initial time, the tumor tissue is the first to show a measurable optical change, indicating that the uptake of dye occurs first in the tumor tissue. The gray-scale bar indicates the relative magnitude of the optical changes in the sequence of difference images. FIGS. 7C and 7D show difference images of the area of interest 4 seconds and 30 seconds, respectively, after dye injection. At these intermediate stages dye appears to collect in both normal and tumor tissue. FIGS. 7E and 7F show difference images of the area of interest 1 minute and 5 minutes, respectively, after injection of dye. At these later times, it becomes clear that dye is still collecting in tumor tissue even though it is being cleared from normal tissue.

The optical signals begin to change within the first 2–3 seconds after dye injection and peak 6 seconds after injection in all three areas, tumor tissue, tumor-surround and normal brain. However, the three different tissue types are differentiated by the rate of rise over the first four seconds, the peak optical change reached, and the eventual plateau that occurs after the first 30 seconds. The tumor tissue had a significantly greater peak percentage difference change than the tumor surround which in turn had a greater peak percentage different change than the normal brain. For example, following maximization of the gain and offset on the camera controls, the peak percentage difference changes were as follows: tumor 40.5±9.6%; tumor surround 16.4±6.8%; and normal brain 9.7±4.7%.

Figure 8:
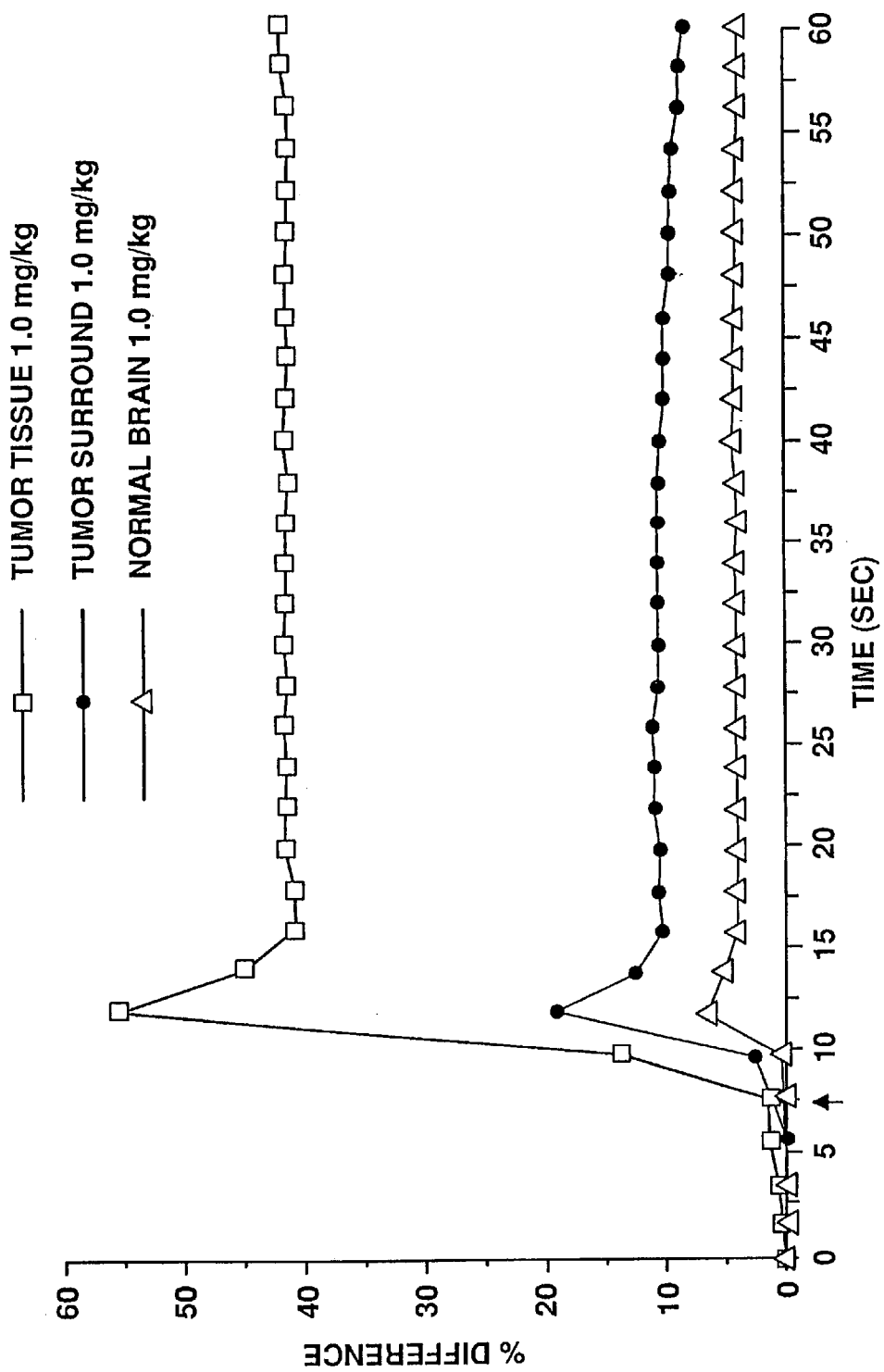
FIG. 8 shows changes in optical properties over time due to dye uptake and clearance in tumor vs. non-tumor tissue. Specifically, this is a plot of an average of the percentage change in optical properties over time averaged over the spatial areas indicated by boxes 1, 2, and 3 in FIG. 7A. The change in optical properties is a function of the concentration of dye in the tissue at a particular time. The graphs labeled "tumor tissue", "tumor surround" and "normal brain" are plots of the change in optical properties over time within boxes 1, 2 and 3, respectively, from FIG. 7A.

FIG. 8 is a plot of an average of the percentage change in optical properties over time averaged over the spatial areas indicated by boxes 1, 2, and 3 from FIG. 7A. The change in optical property is a function of the concentration of dye in the tissue at a particular time. The graphs labeled "tumor tissue", "tumor surround" and "normal brain" are plots of the change in optical properties over time within boxes 1, 2, and 3, respectively, from FIG. 7A. These data, as well as those from FIG. 7, show that the inventive method and device is able to distinguish not only tumor from non-tumor tissue, but also tumor-surround areas which contain varying densities of tumor versus normal cells.

Since the peak optical change was always reached 4–6 seconds after dye injection, there was also a significantly faster rate of optical change in the tumor tissue compared to the tumor surround or the normal brain. A more rapid onset of dye perfusion into the tumor tissue was displayed as a faster time course. The tumor tissue had a more rapid and greater rise time than either the tumor surround or normal brain ($p<0.01$).

In 13 of 14 animals there was a prolonged increase (>2 min) in the optical signal in the tumor after the normal and tumor surround tissue had returned to baseline. Finally, even the normal and tumor surround tissue were significantly different in dye uptake (rise time: normal 2.4%/sec; tumor surround 4.0%/sec). Therefore, the dynamic features of dye uptake and clearance are critical for determining the type of tissue when imaging resection margins.

Figure 9A:
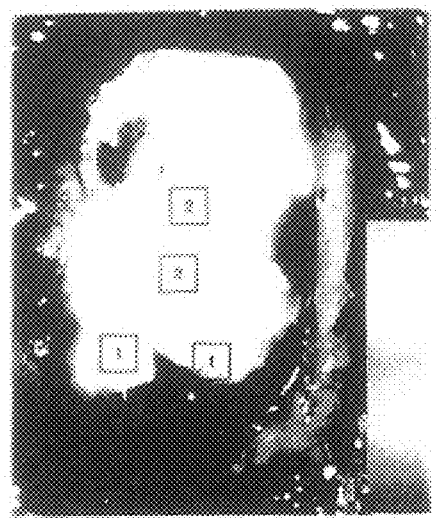
FIGS. 9A–9D demonstrate use of optical imaging of dye uptake to reveal residual traces of tumor cells in resected tumor margins. This is a continuation of the study on the same animal shown in FIGS. 5 through 8.
Figure 9B:
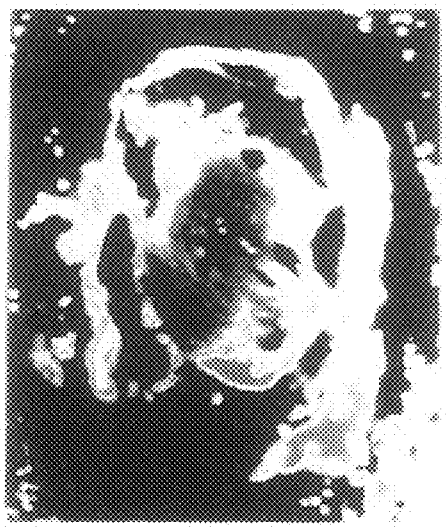
Figure 9C:
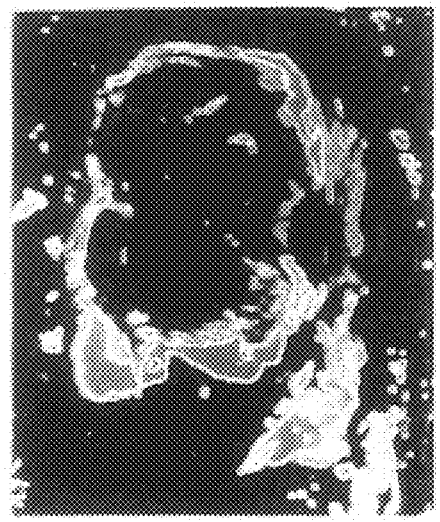
Figure 9D:
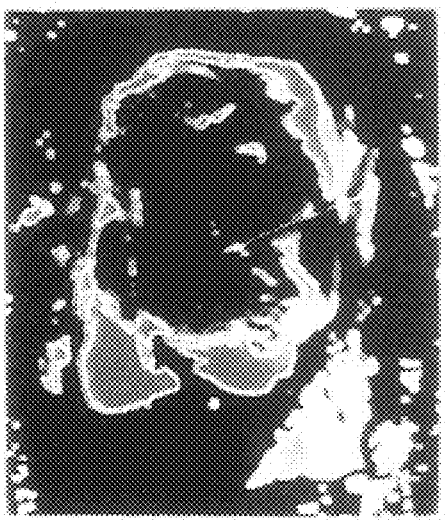

The rat glioma model also provided an opportunity to image resection margins once all visible tumor had been removed. FIG. 9A shows a higher magnification image of the left hemisphere tumor margin of the animal after the tumor had been resected. Boxes 1 overlay areas that contained small traces of residual tumor cells, and boxes 2 overlay areas that contained only normal tissue. The gray-scale bar indicates the magnitude of optical change in the difference images. FIGS. 9B, 9C, and 9D show difference images of the tumor margin 4, 30, and 60 seconds after intravenous dye injection, respectively. Minute biopsies were taken from areas that showed preferred dye containment and from areas from which the dye cleared rapidly. These biopsies were analyzed blindly and later correlated to the location from which the biopsies were taken. Those biopsies taken from areas which cleared dye were shown to contain only normal cells, whereas biopsies taken from areas which sequestered dye were shown to contain tumor cells.

The more rapid rate of rise seen in cortical surface imaging was still present for the resection margins that were positive for tumor compared to normal brain. Again, significant differences between the tumor and the normal brain existed for the rate of rise, peak optical change, and plateau 60 seconds after dye injection (all $p<0.01$). FIGS. 6–9 demonstrate that the inventive method and device can be used in combination with multiple injections of dye for repeated application throughout a tumor resection surgery (in this case, 4 separate injections of dye were given). Furthermore, extremely small islands of residual tumor can be mapped within the tumor margins.

Sensitivity and specificity of optical imaging was determined for 34 samples (n=12 animals). Of 15 biopsy sites deemed negative for tumor by optical imaging, 14 of the 15 were clear of tumor by histological analysis (sensitivity 93%). Most of the specimens that were negative for tumor were taken from the posterior wall of the tumor resection cavity or the depth of the cavity (where the hippocampus or denate gyrus were frequently biopsied). Of 19 biopsy sites deemed positive for tumor by optical imaging, 17 of the biopsy specimens were read as positive for tumor (specificity 89.5%). The two sites that were negative for tumor on histology but positive for tumor by optical imaging had increased cellularity but were deemed negative for tumor because there was no focus of tumor tissue present. The overall significance of these results are $p<0.001$.

Figure 10:
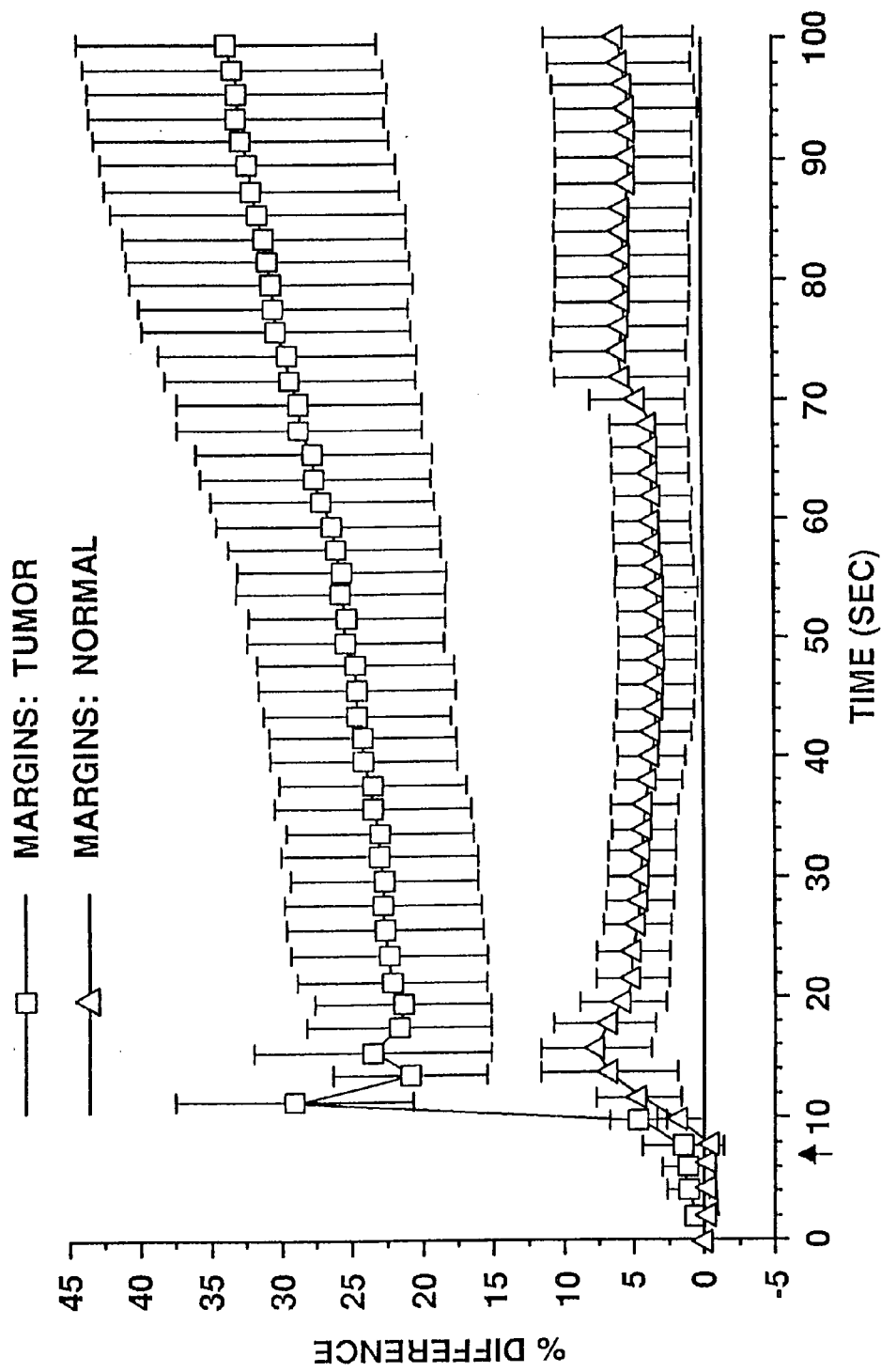
FIG. 10 shows changes in optical properties due to dye uptake and clearance in tumor vs. non-tumor tissue. Specifically, this is a plot of an average of the percentage change in optical properties over time averaged over the spatial areas indicated by boxes 1 and 2 from FIG. 9A. The increase in absorption is a function of the concentration of dye in the tissue at a particular time. The graphs labeled "margins: tumor " and "margins:normal" are plots of the change in optical properties over time within boxes 1 and 2, respectively, from FIG. 9A. These data, as well as those from FIG. 9, show that the inventive device and method are able to distinguish tumor from non-tumor tissue within tumor margins with extremely high spatial resolution.

FIG. 10 shows changes in optical properties due to dye uptake and clearance in tumor vs. non-tumor tissue. Specifically, this is a plot of an average of the percentage change in optical properties over time averaged over the spatial areas indicated by boxes 1 and 2 from FIG. 9A. The increase in absorption is a function of the concentration of dye in the tissue at a particular time. The graphs labeled "margins: tumor" and "margins: normal", are plots of the changes in optical properties over time within boxes 1 and 2, respectively, from FIG. 9A. These data, as well as those from FIG. 9, show that the inventive device and method are able to distinguish tumor from non-tumor tissue within tumor margins with extremely high spatial and temporal resolution.

EXAMPLE 6

A series of experiments was performed using the rat glioma model described in Example 5 to investigate whether the inventive methods and device could image tumor tissue through an intact skull and through intact skin prior to or after surgery. Imaging of tumor tissue was attempted through the intact skull of the rat. The extent of tumor identified was not as accurate as with the cortex exposed. However, the area lying beneath the skull with tumor tissue was easily identified and localized, and continued to concentrate dye after several minutes.

After dye injection, the area of the tumor initially demonstrated a much larger signal than the normal brain of the contralateral hemisphere. One minute after dye injection, the dye had been cleared from the normal brain and the only residual signal remained in tumor tissue and the sagittal/transverse sinuses.

Figure 5A:
FIGS. 5A–5D show non-invasive imaging of dye dynamics and identification of glioma through the intact cranium.
Figure 5B:
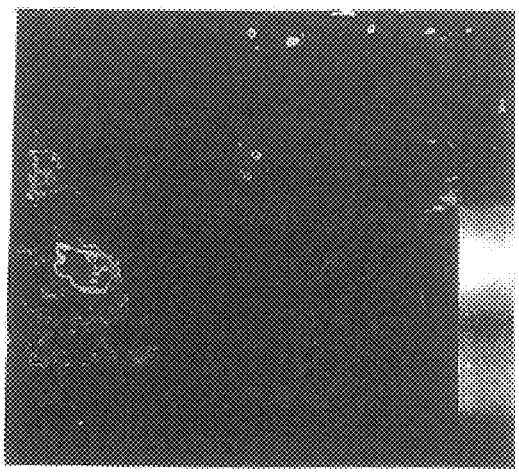
Figure 5C:
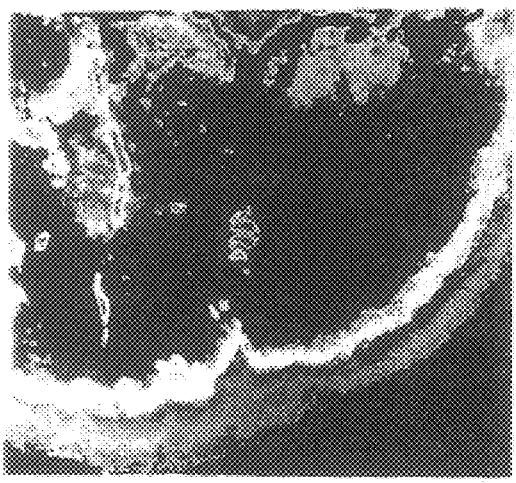
Figure 5D:

FIG. 5A is a gray-scale image of the cranial surface of a rat. The sagittal suture runs down the center of the image. Tumor cells had been injected into the left side some days earlier so that this animal had developed a glioma on the left hemisphere of its brain. The right hemisphere was normal. Box 1 lies over the suspected region of brain tumor, and box 2 lies over normal tissue. FIG. 5B is a difference image 1 second after indocyanine green dye had been intravenously injected into the animal. The region containing tumor tissue becomes immediately visible through the intact cranium. FIG. 5C shows that the dye can be seen to profuse through both normal and tumor tissue 5 seconds after dye injection. FIG. 5D shows that 1 minute after dye injection, the normal tissue has cleared the dye, but dye is still retained in the tumor region. The concentration of dye in the center of this difference image is dye circulating in the sagittal sinus.

Figure 6:
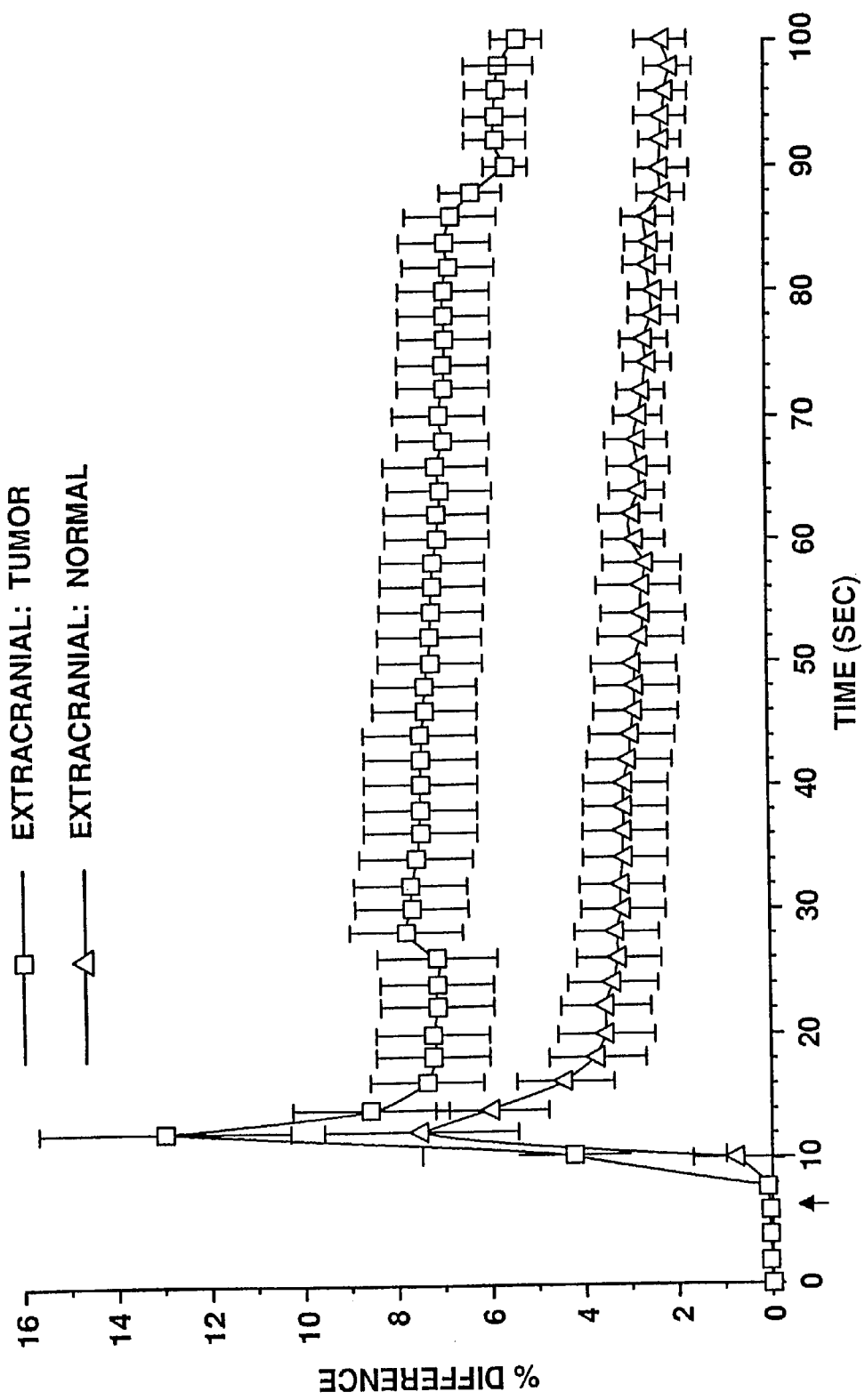
FIG. 6 illustrates the change in optical properties over time due to dye uptake and clearance in tumor vs. non-tumor tissue through the intact skull. Specifically, this is a plot of an average of the percentage change in optical properties over time averaged over the spatial areas indicated by boxes 1 and 2 from FIG. 5A. The change in signal is a function of the concentration of dye in the tissue at a particular time. The graphs labeled "extracranial: tumor" and "extracranial: normal" show the dynamics of the change in optical properties over time within boxes 1 and 2, respectively, from FIG. 5A.

The time course of optical changes imaged through the cranium from ten runs in four animals are shown in FIG. 6. The optical changes were determined by the average optical change in a box placed directly over the tumor and over the normal hemisphere. The change in optical properties is a function of the concentration of dye in the tissue at a particular time. The graph labeled "extracranial tumor" is a plot of the dynamics of the absorption changes within box 1 from FIG. 5A. The graph labeled "extracranial: normal" is a plot of the dynamics of the absorption change within box 2 from FIG. 5A. The peak optical changes for the tumor imaged through the cranium were 13.1±3.9% which was significantly greater compared to those of normal brain of 7.8±2.3% (p<0.01). The plateau phase 60 seconds after dye injection was also significantly greater in tumor tissue (40.5±9.6%) compared to normal brain (3.1±0.7%) (p<0.01).

EXAMPLE 7

This example illustrates various methods for enhancing images obtained from tumor tissue using multiple wavelength and/or laser illumination, and a method for extracting three-dimensional information using multiple wavelengths. We expose a region of cortex in an anesthetized rat, in which we have induced tumor growth. First, illuminating with white light from a tungsten filament lamp, we acquire a first sequence of difference images prior to and following administration of a dye, such as indocyanine green or Evans blue, into the area of interest. Next, we acquire second and third difference image sequences, following the identical procedure for the first sequence, except that in the second sequence, the cortex is illuminated with 690 nm and in the third sequence with 510 nm light. The change in wavelengths is accomplished by placing either a 690±10 nm cutoff filter or a 510±10 nm cutoff filter between the light-source and the area of interest.

We compute the contrast-enhanced image by first ratioing a control 690 nm image with a control 510 nm image. Second, we ratio a 690 nm image following dye administration with the corresponding 510 nm image. We then combine the ratio images to compute the percentage difference image. In this manner, the noise has been significantly reduced, hence the signal/noise ratio has been significantly increased.

Next, we extract depth information from the multiple wavelength images that we have acquired as follows. Longer wavelength light penetrates to a greater depth through the cortex than shorter wavelength light. Hence, the 690 nm image penetrates the cortex to x mm, and the 510 nm image to y mm where x<y. We subtract the 610 nm image from the 510 nm image, showing an "optical wedge" containing information from a depth of (x−y) mm to x mm within the cortical tissue. By using a series of other cutoff filters, we acquire a sequence of images containing information from many different depths of the cortex. Thus, it is possible to acquire three-dimensional information.

We claim:

1. A method for detecting margins and dimensions of tumor tissue in an area of interest, comprising:
   (a) illuminating the area of interest with an illumination source emitting electromagnetic radiation (emr) having at least one wavelength which interacts with a dye;
   (b) administering the dye to the area of interest;
   (c) detecting one or more optical properties of the area of interest subsequent to administration of the dye and thereby acquiring a subsequent data set representing the one or more optical properties of the area of interest subsequent to the administration of the dye;
   (d) comparing the subsequent data set with a control data set representing the one or more optical properties of the area of interest prior to administration of the dye to produce a comparison data set; and
   (e) distinguishing tumor from non-tumor tissue in the area of interest based on differences in the one or more optical properties evidenced in the comparison data set, the differences in the one or more optical properties "representing" different dynamics of dye perfusion in tumor and non-tumor tissue.

2. A method according to claim 1, wherein the dye is selected from the group consisting of indocyanines, fluoresceins, hematoporphyrins, fluoresdamines and combinations thereof.

3. A method according to claim 1, wherein the area of interest is located underneath at least one of intact skin and bone and the emr is in the infrared region.

4. A method according to claim 1, step (c), wherein detecting is carried out with a CCD apparatus.

5. A method according to claim 1, additionally comprising compensating for movement in the area of interest by aligning markers indicating corresponding spatial locations in the control and subsequent data sets to produce the comparison data set.

6. A method according to claim 1, wherein the control data set is a control image, the subsequent data set is a subsequent image, and the comparison data set is a comparison image.

7. A method according to claim 6, wherein the control and subsequent images are obtained as analog video signals and the analog video signals are amplified and spread across a full dynamic range.

8. A method according to claim 6, additionally comprising mapping different pixel values comprising the comparison image to color values to enhance the contrast of the comparison image.

9. A method according to claim 1, wherein the optical property detected is selected from the group consisting of: reflection; refraction; diffraction; absorption; scattering; birefringence; refractive index; and Kerr effect.

10. A method according to claim 1, wherein the comparison data set is displayed in a graphical format.

11. A method according to claim 1, wherein the subsequent data set comprises a plurality of subsequent data points representing optical property values corresponding to specified, spatially resolved subsequent locations in the area of interest, the control data set comprises a plurality of control data points representing optical property values corresponding to specified, spatially resolved control locations in the area of interest, wherein the subsequent locations and the control locations are at the same spatial locations in the area of interest.

12. A method according to claim 1, wherein the subsequent data set and the control data set each include a plurality of data points that are spatially resolved with respect to the area of interest, and the comparison data set compares control and subsequent data points having the same spatial location in the area of interest.

13. A method of grading or characterizing tumor tissue located in an area of interest, comprising:
   (a) illuminating the area of interest with an illumination source emitting electromagnetic radiation (emr) having at least one wavelength which interacts with a dye;
   (b) administering the dye to the area of interest;
   (c) detecting one or more optical properties of the area of interest subsequent to administration of the dye and thereby acquiring a subsequent data set representing the one or more optical properties of the area of interest subsequent to administration of the dye;
   (d) comparing the subsequent data set with a control data set representing the one or more optical properties of the area of interest to produce a comparison data set; and
   (e) differentiating grades of tumors in the area of interest based on differences in the one or more optical properties evidenced in the comparison data set, the differences in the one or more optical properties representing different dynamics of dye perfusion in different grades of tumor tissue.

14. A method according to claim 13, wherein the dye is selected from the group consisting of indocyanines, fluoresceins, hematoporphyrins, fluoresdamines and combinations thereof.

15. A method according to claim 13, wherein the area of interest is located underneath at least one of intact skin and bone and the emr is in the infrared region.

16. A method according to claim 13, step (c), wherein detecting is carried out with a CCD apparatus.

17. A method according to claim 13, additionally comprising compensating for movement in the area of interest by aligning markers indicating corresponding spatial locations in the control and subsequent data sets to produce the comparison data set.

18. A method according to claim 13, wherein the control data set is a control image, the subsequent data set is a subsequent image, and the comparison data set is a comparison image.

19. A method for detecting the presence of tumor tissue in an area of interest suspected to contain tumor tissue comprising:

(a) illuminating the area of interest with at least two different wavelengths of electromagnetic radiation (emr);

(b) obtaining a sequence of control data sets corresponding to the area of interest for each wavelength of emr;

(c) administering a dye to the area of interest;

(d) obtaining a sequence of subsequent data sets corresponding to the area of interest for each wavelength of emr following administration of the dye; and (e) obtaining a series of comparison data sets for each wavelength of emr by subtracting one of the control data set and the subsequent data set from the other of the control data set and the subsequent data set.

20. A method according to claim 19, additionally comprising obtaining an enhanced comparison data set by ratioing a first comparison data set to a second comparison data set.

21. A method according to any of claims 1, 13, 11 or 19, wherein the optical detector is a video camera.

22. A method according to any of claims 1, 13, 11 or 19, additionally comprising amplifying portions of the control data set to enhance the contrast of the comparison data set.

23. A method according to claim 19, additionally comprising displaying the comparison data set in a visual image format.

24. A method according to claim 11, wherein each of the control data points and the subsequent data points is detected using a CCD apparatus.

25. A method according to claim 11, additionally comprising acquiring a plurality of control data sets and a plurality of subsequent data sets, averaging the plurality of each of the control data sets to produce an averaged control data set, and averaging the plurality of each of the subsequent data sets, and comparing the averaged subsequent data set with the averaged control data set.

26. A method according to claim 11 or 19, wherein the area of interest is located underneath at least one of intact skin and bone, and the illuminating and detecting takes place through the at least one of intact skin and bone.

27. A method according to claim 11 or 19, wherein the comparison data set is an image and processing provides an enhanced contrast color image.

28. A method according to claim 11, wherein comparing the subsequent data set with a control data set to distinguish tumor from non-tumor tissue in each of the spatially resolved locations in the area of interest distinguishes between positive-going and negative-going changes.

29. A method according to any of claims 1, 13 or 19, comprising illuminating the area of interest with uniform intensity emr.

30. A method according to any of claims 1, 13 or 19, comprising illuminating the area of interest with non-continuous illumination.

31. A method according to any of claims 1, 13 or 19, comprising illuminating the area of interest with an illumination source using at least one of the following: amplitude modulated; frequency modulated; and phase modulated techniques.

32. A method according to any of claims 1, 13, 11 or 19, comprising producing the comparison data set in real-time.

33. A method according to claim 11, wherein one or more spatially resolved locations in the area of interest is detected using at least one of the following detectors: at least one photodiode; at least one photomultiplier tube; at least one camera; at least one video camera; and at least one CCD camera.

34. A method according to claim 11, wherein one or more spatially resolved locations in the area of interest is is illuminated using at least one of the following sources: a tungsten-halogen lamp; a laser; a laser diode; and a light-emitting diode.

35. A method according to any of claims 1, 13, or 19, wherein at least one blood characteristic is monitored simultaneously with differences in the dynamics of dye perfusion in tumor and non-tumor tissue in the area of interest.

36. A method according to any of claims 1, 13, or 19, wherein the area of interest is illuminated using at least one optical fiber operably connected to an emr source.

37. A method according to any of claims 1, 13, or 19, wherein the area of interest is detected using at least one optical fiber operably connected to an optical detector.

38. A method according to any of claims 1, 13, 11 or 38 wherein the area of interest is breast tissue.

39. A method according to any of claims 1, 13, 11 or 19, wherein the dye is indocyanine green.

40. A method according to any of claims 1, 13 or 19, wherein the dye is conjugated to a targeting molecule.

* * * * *